(12) United States Patent
Bogue

(10) Patent No.: US 9,149,959 B2
(45) Date of Patent: Oct. 6, 2015

(54) MANUFACTURING OF SMALL FILM STRIPS

(75) Inventor: Beuford A. Bogue, New Carlisle, IN (US)

(73) Assignee: MONOSOL RX, LLC, Warren, NJ (US)

( * ) Notice: Subject to any disclaimer, the term of this patent is extended or adjusted under 35 U.S.C. 154(b) by 650 days.

(21) Appl. No.: 12/909,995

(22) Filed: Oct. 22, 2010

(65) Prior Publication Data
US 2012/0100202 A1 Apr. 26, 2012

(51) Int. Cl.
| | |
|---|---|
| A23L 1/00 | (2006.01) |
| A23G 3/02 | (2006.01) |
| B29C 41/28 | (2006.01) |
| A61K 9/00 | (2006.01) |
| A61K 9/70 | (2006.01) |
| B29C 47/00 | (2006.01) |
| B29C 47/02 | (2006.01) |
| B29C 47/06 | (2006.01) |
| B29C 47/08 | (2006.01) |
| B29C 31/06 | (2006.01) |

(52) U.S. Cl.
CPC ............ *B29C 41/28* (2013.01); *A61K 9/006* (2013.01); *A61K 9/0014* (2013.01); *A61K 9/7007* (2013.01); *A61K 9/7084* (2013.01); *B29C 47/0021* (2013.01); *B29C 47/0066* (2013.01); *B29C 47/025* (2013.01); *B29C 47/065* (2013.01); *B29C 47/0816* (2013.01); *B29C 31/06* (2013.01); *B29C 47/0004* (2013.01)

(58) Field of Classification Search
None
See application file for complete search history.

(56) References Cited

U.S. PATENT DOCUMENTS

| | | | |
|---|---|---|---|
| 5,360,629 A | 11/1994 | Milbourn et al. | |
| 5,965,154 A | 10/1999 | Haralambopoulos | |
| 6,344,088 B1 | 2/2002 | Kamikihara et al. | |
| 7,425,292 B2 * | 9/2008 | Yang et al. | 264/172.19 |
| 2005/0019588 A1 | 1/2005 | Berry et al. | |
| 2006/0169205 A1 | 8/2006 | Liu et al. | |
| 2007/0281003 A1 | 12/2007 | Fuisz et al. | |
| 2009/0181075 A1 | 7/2009 | Gordon et al. | |
| 2010/0092545 A1 | 4/2010 | Yang et al. | |
| 2012/0263865 A1 | 10/2012 | Bogue | |

FOREIGN PATENT DOCUMENTS

| | | |
|---|---|---|
| CN | 101668519 A | 3/2010 |
| WO | 93/05212 A2 | 3/1993 |

OTHER PUBLICATIONS

Google search page for NPL search; added Feb. 7, 2013.*

(Continued)

*Primary Examiner* — Jeffery T Palenik
(74) *Attorney, Agent, or Firm* — Hoffmann & Baron, LLP

(57) ABSTRACT

The present invention relates to methods and apparatuses for forming films. In particular, the present invention relates to the formation of films on a substrate via the use of individual pumps to deposit individual wet film products onto a substrate. A method of forming film products includes: providing a reservoir housing a film forming matrix, pumps in association with the reservoir, and orifices; feeding the wet film forming matrix from the reservoir to the pumps; dispensing the film forming matrix from each of the pumps through an orifice; and depositing wet film products onto a substrate. An apparatus for forming film strips includes: (a) a reservoir for housing a film forming matrix; (b) pumps associated with the reservoir; (c) a plurality of orifices, with each orifice being associated with a pump; (d) a substrate; and (e) a means for moving the substrate through the apparatus.

77 Claims, 4 Drawing Sheets

(56) References Cited

OTHER PUBLICATIONS

Pneumatic Driven Liquid Pumps; brochure published by Haskel Milton Roy on Oct. 2009; downloaded Feb. 7, 2013 (24 pp).*
Google search result for definition of "manifold": Vocabulary.com; 3 pages; accessed Sep. 22, 2013.*
International Search Report PCT/US2011/57233 Dated Feb. 10, 2012.
Written Opinion PCT/US2011/57233 Dated Feb. 10, 2012.
EPO Communication dated Sep. 11, 2014, with accompanying extended European search report including supplementary European search report and European search opinion for EP 11 835 203.8, Date of Completion of Search: Jul. 31, 2014.
Chinese Office Action (in Chinese) for Chinese Application No. 201180056133.5 dated Nov. 15, 2014.

* cited by examiner

MANUFACTURING OF SMALL FILM STRIPS

FIELD OF THE INVENTION

The present invention relates to methods for forming films. In particular, the present invention relates to the formation of films, in particular, small film strips, on a substrate via the use of individual pumps.

BACKGROUND OF THE INVENTION

The use of films for the administration of active agents, such as pharmaceuticals, cosmetic and other materials, is becoming increasingly popular. Such films should have a fairly uniform size, and a substantially uniform distribution of components. The substantially uniform distribution of components is quite important when the films include pharmaceutical components, to ensure accurate dosages.

Films may be formed in any desired fashion, and in some cases it may be useful to form a film on the surface of a substrate. The use of a substrate to form film not only provides ease in processing but may also aid in packaging the film products. Typically, a wet film-forming matrix is deposited onto the surface of a substrate, and then dried to form the resulting film, which is then sized and cut into individual film strip products. Unfortunately, however, such typical processes result in a great deal of wasted film due to the sizing and cutting process.

Further, traditional processing methods use one pumping mechanism with multiple slot dies or other orifices. Such methods have a tendency to dispense a wet film forming matrix unevenly through orifices, giving irregular and non-uniform dosages. In addition, in the case of film matrices having a high solid or particle content, the orifices may have a tendency to become blocked. The use of one pumping mechanism for multiple orifices may not provide enough pressure to release the blocked orifice, resulting in certain orifices dispensing higher amounts of the film-forming matrix. Thus, the end result of such traditional processing is a potential for uneven dosaging and products that lack compositional uniformity.

The present invention seeks to solve the problems incurred with traditional film processing, such as by providing a method that continuously produces film products without the need for sizing the film products, while at the same time providing uniform film dosages.

SUMMARY OF THE INVENTION

In one embodiment of the present invention, there is provided a method of forming a plurality of individual film products, including the steps of: (a) providing a reservoir housing a film forming matrix; (b) providing a plurality of individual volumetric pumps in association with the reservoir; (c) providing a plurality of orifices, where each orifice is associated with an individual volumetric pump; (d) feeding the film forming matrix from the reservoir to the individual volumetric pumps; (e) dispensing a predetermined amount of the film forming matrix from each of the volumetric pumps through an orifice associated therewith; and (f) extruding an individual wet film product onto a substrate.

Other embodiments of the present invention may provide a method of forming a plurality of individual film strips, including the steps of: (a) providing a reservoir housing a film forming matrix; (b) providing a plurality of individual metering pumps in association with the reservoir; (c) providing a plurality of orifices, where each orifice is associated with an individual metering pump; (d) feeding the film forming matrix from the reservoir to the plurality of individual metering pumps; (e) dispensing a predetermined amount of the film forming matrix from each of the metering pumps through an orifice associated therewith; and (f) extruding an individual wet film strip through the orifice onto a substrate.

In another embodiment of the present invention, there is provided an apparatus for forming a plurality of individual film products, including: a reservoir for housing a film forming matrix; a plurality of individual volumetric pumps associated with the reservoir; a plurality of orifices, each orifice being associated with a volumetric pump; a substrate; and a means for moving the substrate through the apparatus.

In yet another embodiment of the present invention, there is provided a method of forming a plurality of individual film patches, including the steps of: (a) providing a substrate including a first polymeric material, the substrate having a top surface, where the substrate continuously moves in a first direction; (b) providing a reservoir housing a film forming matrix, the film forming matrix including a second polymeric material and an active; (c) providing a plurality of individual volumetric pumps in association with the reservoir; (d) providing a plurality of orifices, where each orifice is associated with an individual volumetric pump, where each orifice is separated from each other by a gap; (e) feeding the film forming matrix from the reservoir to the individual volumetric pumps; (f) dispensing a predetermined amount of the film forming matrix from each of the volumetric pumps through an orifice associated therewith; (g) extruding the predetermined amount of the film forming matrix onto the top surface of the substrate as the substrate moves in the first direction to form a plurality of individual wet film products; and (h) drying the individual wet film products to form a plurality of patches including a first layer of substrate and a second layer of dried film products.

DETAILED DESCRIPTION OF THE INVENTION

Figure 1:
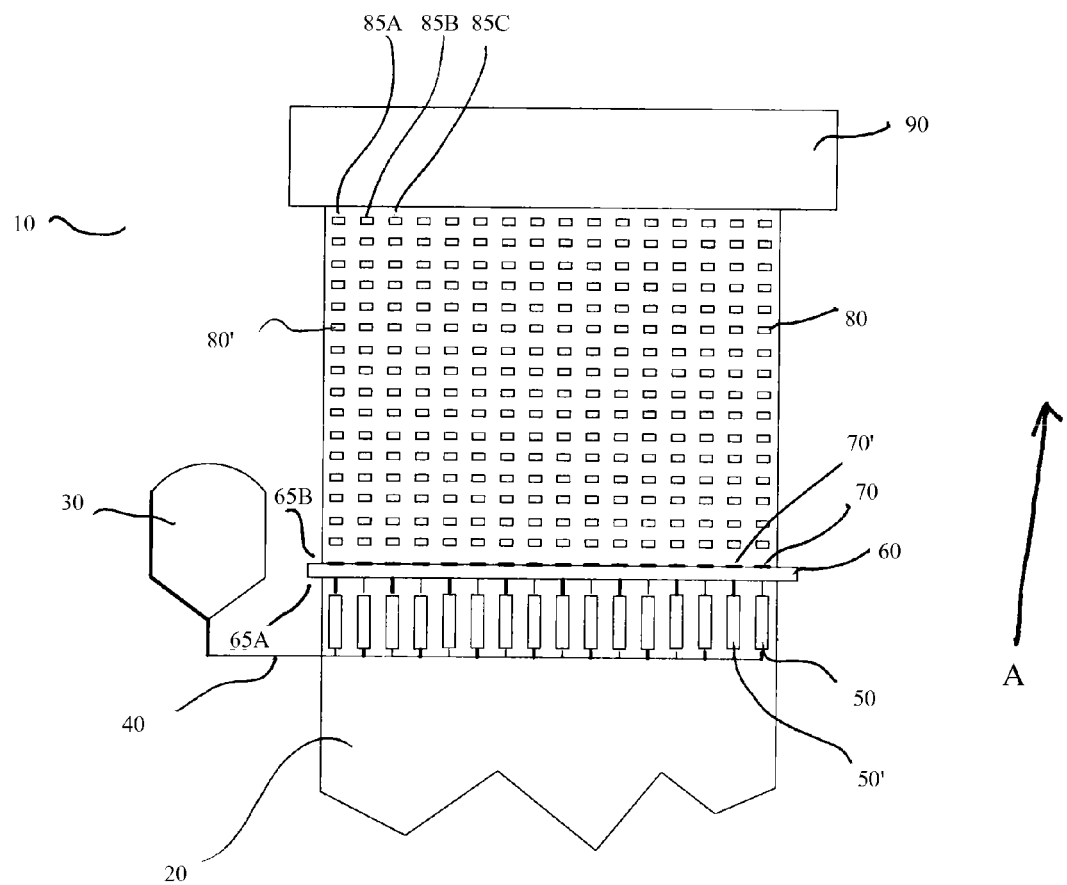
FIG. 1 is a depiction of one embodiment of the present invention that is capable of forming individual film products.

The present invention relates to methods and apparatuses designed for forming film products, including film products that include at least one active composition. Specifically, the invention relates to methods of forming film products on a substrate, while maintaining the uniformity of content and the structural integrity of the individual film product. Further, the invention provides a method and apparatus for forming film products that minimizes the amount of waste typically required in film processing. Film systems embody a field of technology that has major advantages in areas of administering drug, medicament, and various other active and agent delivery systems to an individual in need thereof. In order to provide a desirable final product that exhibits advantageous characteristics and desirable properties, including uniformity of content, the processing and manufacturing of film strips and film technology is technologically demanding and cumbersome.

As used herein, the terms "pharmaceutical", "medicament", "drug" and "active" may be used interchangeably, and refer to a substance or composition useful for the prevention or treatment of a condition. The terms may include pharmaceuticals, neutraceuticals, cosmetic agents, biologic agents, bioeffective substances, and the like.

It will be understood that the term "film" includes delivery systems of any thickness, including films and film strips, sheets, discs, wafers, and the like, in any shape, including rectangular, square, or other desired shape. The film may be in the form of a continuous roll of film or may be sized to a desired length and width. The films described herein may be any desired thickness and size suitable for the intended use. For example, a film of the present invention may be sized such that it may be placed into the oral cavity of the user. Other films may be sized for application to the skin of the user, i.e., a topical use. For example, some films may have a relatively thin thickness of from about 0.1 to about 10 mils, while others may have a somewhat thicker thickness of from about 10 to about 30 mils. For some films, especially those intended for topical use, the thickness may be even larger, i.e., greater than about 30 mils. In addition, the term "film" includes single-layer compositions as well as multi-layer compositions, such as laminated films, coatings on films and the like. The composition in its dried film form maintains a uniform distribution of components through the processing of the film. Films may include a pouch or region of medicament between two films.

The term "patch" as used herein is intended to include multi-layered film products, where the first layer (or "backing layer") is a film product that has a slower rate of dissolution than the second layer (or "active layer"). Patches described herein generally include the first and second layers adhered or laminated to each other, where the second layer has a smaller length and/or width of the first layer, such that at least a portion of the surface of the first layer is visible outside of the second layer (including, but not limited to, the design shown in FIG. 3B and described in further detail herein).

Films formed by the present invention may be suitable for administration to at least one region of the body of the user, such as mucosal regions or regions within the body of the user, such as on the surface of internal organs. In some embodiments of the invention, the films are intended for oral administration. In other embodiments, the films are intended for topical administration. As used herein, the term "topical agent" is meant to encompass active agents that are applied to a particular surface area. For example, in one embodiment, a topical agent is applied to an area of the skin. In other embodiments, the topical agent may also be applied to mucosal areas of the body, such as the oral (e.g., buccal, sublingual, tongue), vaginal, ocular and anal areas of the body. In still other embodiments, the topical agent is applied to an internal organ or other body surface of the user, such as during surgery, where the agent may be removed or left within the body after surgery is complete. In other embodiments, a topical agent is applied to a hard surface, such as a particular surface area in need of treatment. In other embodiments, the films of the present invention are ingestible, and are intended to be placed in the mouth of the user and swallowed as the film disintegrates.

The medicament may be dispersed throughout the film, or it may be deposited onto one or more surfaces of the film. In either way, it is desirable that the amount of medicament per unit area is substantially uniform throughout the film. The "unit area" is intended to include a suitable unit area, such as the area of one typical dosage unit. It is desired that the films of the present invention include a uniformity of component distribution throughout the volume of a given film. Such uniformity includes a substantially uniform amount of medicament per unit volume of the film, whether the medicament is within the matrix of the film or coated, laminated, or stabilized on one or more surfaces thereof. When such films are cut into individual units, the amount of the agent in the unit can be known with a great deal of accuracy. For the films formed herein, it is understood by one of ordinary skill in the art that the resulting film is not required to be exactly 100% uniform. All that is required is that the film be "substantially uniform", i.e., a slight amount of non-uniformity is understood to be acceptable. "Substantially uniform" may include, for example, a film that is about 90% uniform in content from one region of the film to another, or a film that is about 95% uniform in content from one region of the film to another, and most desirably about 99% uniform in content from one region of the film to another.

It is desirable that any individual film products formed by the present invention (i.e., products having a substantially similar mass and volume) be substantially uniform in content with respect to each other. That is, the individual film products (including individual dosages of approximately equal sizes) formed by the present invention should have approximately the same content composition as each other film product. Of course, it will be understood that some deviation is to be expected during the manufacturing process, but desirably the individual film products should be at least 90% uniform in content with respect to each other. In other words, "substantially uniform" may mean that individual film products should vary by no more than about 10% with respect to each other. In some embodiments, "substantially uniform" may mean that individual film products should vary by no more than about 5% with respect to each other.

Uniformity of medicament throughout the film is important in administering an accurate and effective dose of medicament to a user. Various methods of forming uniform films, as well as various polymers, additives and fillers, may be used, including those methods and materials described in U.S. Pat. Nos. 7,425,292, 7,357,891 and 7,666,337, which are herein incorporated by reference in their entireties. Any number of active components or pharmaceutical agents may be included in the films discussed herein. The active component(s) may be disposed within any layer of film products formed herein or they may be placed onto one or more surfaces of the film products.

Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulants, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, uterine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (commercially available as Oxycontin®); ibuprofen (commercially available as Motrin®, Advil®, Motrin Children's®, Motrin IB®), Advil Children's®, Motrin Infants'®, Motrin Junior®, Ibu-2®, Proprinal®, Ibu-200®, Midol Cramp Formula®, Bufen®, Motrin Migraine Pain®, Addaprin® and Haltran®), aspirin (commercially available as Empirin®, Ecotrin®, Genuine Bayer®, and Halfprin®), acetaminophen (commercially available as Silapap Infant's®, Silapap Children's®, Tylenol®, Tylenol Children's®, Tylenol Extra Strength®, Tylenol Infants' Original®, Tylenol Infants'®, Tylenol Arthritis®, T-Painol®, Q-Pap®, Cetafen®, Dolono®, Tycolene®, APAP®, and Aminofen®), and combinations thereof that may optionally include caffeine. Other pain relieving agents may be used in the present invention, including meperidine hydrochloride (commercially available as Demerol®), capsaicin (commercially available as Qutenza®), morphine sulfate and naltrexone hydrochloride (commercially available as Embeda®), hydromorphone hydrochloride (commercially available as Dilaudid®), propoxyphene napsylate and acetaminophen (commercially available as Darvocet-N®), Fentanyl (commercially available as Duragesic®, Onsolis®, and Fentora®), sodium hyaluronate (commercially avialble as Euflexxa®), adalimumab (commercially available as Humira®), sumatriptan succinate (commercially available as Imitrex®), fentanyl iontophoretic (commercially available as Ionsys®), orphenadrine citrate (commercially available as Norgesic®), magnesium salicylate tetrahydrate (commercially available as Novasal®), oxymorphone hydrochloride (commercially available as Opana ER®), methocarbamol (commercially available as Robaxin®), carisoprodol (commercially available as Soma®), tramadol hydrochloride (commercially available as Ultracet® and Ultram®), morphine sulfate (commercially available as MS Contin®), metaxalone (commercially available as Skelaxin®), oxycodone hydrochloride (commercially available as OxyContin®), acetaminophen/oxycodone hydrochloride (commercially available as Percocet®), oxycodone/aspirin (commercially available as Percodan®), hydrocodone bitartrate/acetaminophen (commercially available as Vicodin®), hydrocodone bitartrate/ibuprofen (commercially available as Vicoprofen®), nepafenac (commercially available as Nevanac®), and pregabalin (commercially available as Lyrica®).

The present invention may further include agents such as NSAIDs, including etodolac (commercially available as Lodine®), ketorolac tromethamine (commercially available as Acular® or Acuvail®), naproxen sodium (commercially available as Anaprox®, Naprosyn®), flurbiprofen (commercially available as Ansaid®), diclofenac sodium/misoprostol (commercially available as Arthrotec®), celecoxib (commercially available as Celebrex®), sulindac (commercially available as Clinoril®), oxaprozin (commercially available as Daypro®), piroxicam (commercially available as Feldene®), indomethacin (commercially available as Indocin®), meloxicam (commercially available as Mobic®), mefenamic acid (commercially available as Ponstel®), tolmetin sodium (commercially available as Tolectin®), choline magnesium trisalicylate (commercially available as Trilisate®), diclofenac sodium (commercially available as Voltaren®), diclofenac potassium (commercially available as Cambia® or Zipsor®), and misoprostol (commercially available as Cytotec®). Opiate agonists and antagonists, such as buprenorphine and naloxone are further examples of drugs for use in the present invention.

Other preferred drugs for other preferred active ingredients for use in the present invention include anti-diarrheals such as loperamide (commercially available as Imodium ADC), Imotil®, Kaodene®, Imperim®, Diamode®, QC Anti-Diarrheal®, Health Care America Anti-Diarrheal®, Leader A-D®, and Imogen®), nitazoxanide (commercially available as Alinia®) and diphenoxylate hydrochloride/atropine sulfate (commercially available as Lomotil®), anti-histamines, anti-tussives, decongestants, vitamins, and breath fresheners. Common drugs used alone or in combination for colds, pain, fever, cough, congestion, runny nose and allergies, such as acetaminophen, ibuprofen, chlorpheniramine maleate, dextromethorphan, dextromethorphan HBr, phenylephrine HCl, pseudoephedrine HCl, diphenhydramine and combinations thereof, such as dextromethophan HBr and phenylephrine HCl (available as Triaminic®) may be included in the film compositions of the present invention.

Other active agents useful in the present invention include, but are not limited to alcohol dependence treatment, such as acamprosate calcium (commercially available as Campral®); Allergy treatment medications, such as promethazine hydrochloride (commercially available as Phenergan®), bepotastine besilate (commercially available as Bepreve®), hydrocodone polistirex/chlorpheniramine polistirex (commercially available as Tussionex®), cetirizine hydrochloride (commercially available as Zyrtec®), cetirizine hydrochloride/pseudoephedrine hydrochloride (commercially available as Zyrtec-D®), promethazine hydrochloride/codeine phosphate (commercially available as Phenergan® with Codeine), pemirolast (commercially available as Alamast®), fexofenadine hydrochloride (commercially available as Allegra®), meclizine hydrochloride (commercially available as Antivert®), azelastine hydrochloride (commercially available as Astelin®), nizatidine (commercially available as Axid®), desloratadine (commercially available as Clarinex®), cromolyn sodium (commercially available as Crolom®), epinastine hydrochloride (commercially available as Elestat®), azelastine hydrochloride (commercially available as Optivar®), prednisolone sodium phosphate (commercially available as Orapred ODT®), olopatadine hydrochloride (commercially available as Patanol®), ketotifen fumarate (commercially available as Zaditor®), and montelukast sodium (commercially available as Singulair®); and anti-histamines such as diphenhydramine HCl (available as Benadryl®), loratadine (available as Claritin®), astemizole (available as Hismanal®), nabumetone (available as Relafen®), diphenydramine HCL (available as TheraFlu®) and clemastine (available as Tavist®).

Films of the present invention may further include Alzheimer's treatment medications, such as tacrine hydrochloride (commercially available as Cognex®), galantamine (commercially available as Razadyne®), donepezil hydrochloride (commercially available as Aricept®), rivastigmine tartrate (commercially available as Exelon®), caprylidene (commercially available as Axona®), and memantine (commercially available as Namenda®); anemia medication, such as cyanocobalamin (commercially available as Nascobal®) and ferumoxytol (commercially available as Feraheme®); anesthetics, such as antipyrine with benzocaine (commercially available as Auralgan®, Aurodex® and Auroto®); angina medication, such as amlodipine besylate (commercially available as Norvasc®), nitroglycerin (commercially available as Nitro-Bid®, Nitro-Dur®, Nitrolingual®, Nitrostat®, Transderm-Nitro®), isosorbide mononitrate (commercially available as Imdur®), and isosorbide dinitrate (commercially available as Isordil®); anti-tussives such as guaifensin; anti-Alzheimer's agents, such as nicergoline; and $Ca^H$-antagonists such as nifedipine (commercially available as Procardia® and Adalat®).

Actives useful in the present invention may also include anti-asthmatics, such as albuterol sulfate (commercially available as Proventil®), ipratropium bromide (commercially available as Atrovent®), salmeterol xinafoate (commercially available as Serevent®), zafirlukast (commercially available as Accolate®), flunisolide (commercially available as AeroBid®), metaproterenol sulfate (commercially available as Alupent®), albuterol inhalation (commercially available as Ventolin®), terbutaline sulfate (commercially available as Brethine®), formoterol (commercially available as Foradil®), cromolyn sodium (commercially available as Intal®), levalbuterol hydrochloride (commercially available as Xopenex®), zileuton (commercially available as Zyflo®), fluticasone propionate/salmeterol (commercially available as Advair®), albuterol sulfate/triamcinolone acetonide (commercially available as Azmacort®), dimethylxanthine (commercially available as Theophylline®), and beclomethasone (commercially available as Beclovent®, Beconase®, Qvar®, Vancenase®, Vanceril®); angioedema medication, such as Cl esterase Inhibitor (human) (commercially available as Berinert®) and ecallantide (commercially available as Kalbitor®); and antibacterial medications, such as trimethoprim/sulfamethoxazole (commercially available as Bactrim®), mupirocin (commercially available as Bactroban®), metronidazole (commercially available as Flagyl®), sulfisoxazole acetyl (commercially available as Gantrisin®), bismuth subsalicylate and metronidazole/tetracycline hydrochloride (commercially available as Helidac Therapy®), nitrofurantoin (commercially available as Macrodantin®), norfloxacin (commercially available as Noroxin®), erythromycin ethylsuccinate/Sulfisoxazole acetyl (commercially available as Pediazole®), and levofloxacin (commercially available as Levaquin®).

The present invention may further include one or more antibiotics, including amoxicillin (commercially available as Amoxil®), ampicillin (commercially available as Omnipen®, Polycillin® and Principen®), amoxicillin/clavulanate potassium (commercially available as Augmentin®), moxifloxacin hydrochloride (commercially available as Avelox®), besifloxacin (commercially available as Besivance®), clarithromycin (commercially available as Biaxin®), ceftibuten (commercially available as Cedax®), cefuroxime axetil (commercially available as Ceftin®), cefprozil (commercially available as Cefzil®), ciprofloxacin hydrochloride (commercially available as Ciloxan® and Cipro®), clindamycin phosphate (commercially available as Cleocin T®), doxycycline hyclate (commercially available as Doryx®), dirithromycin (commercially available as Dynabac®), erythromycin (commercially available as E.E.S.®, E-Mycin®, Eryc®, Ery-Tab®, Erythrocin®, and PCE®), erythromycin topical (commercially available as A/T/S®, Erycette®, T-Stat®), gemifloxacin (commercially available as Factive®), ofloxacin (commercially known as Ocuflox®, Floxin®), telithromycin (commercially available as Ketek®), lomefloxacin hydrochloride (commercially available as Maxaquin®), minocycline hydrochloride (commercially available as Minocin®), fosfomycin tromethamine (commercially available as Monurol®), penicillin with potassium (commercially available as Penicillin VK®, Veetids®), trimethoprim (commercially available as Primsol®), ciprofloxacin hydrochloride (commercially available as Proquin XR®), rifampin, isoniazid and pyrazinamide (commercially available as Rifater®), cefditoren (commercially available as Spectracef®), cefixime (commercially available as Suprax®), tetracycline (commercially available as Achromycin V® and Sumycin®), tobramycin (commercially available as Tobrex®), rifaximin (commercially available as Xifaxan®), azithromycin (commercially available as Zithromax®), azithromycin suspension (commercially available as Zmax®), linezolid (commercially available as Zyvox®), benzoyl peroxide and clindamycin (commercially available as BenzaClin®), erythromycin and benzoyl peroxide (commercially available as Benzamycin®), dexamethasone (commercially available as Ozurdex®), ciprofloxacin and dexamethasone (commercially available as Ciprodex®), polymyxin B sulfate/neomycin sulfate/hydrocortisone (commercially available as Cortisporin®), colistin sulfate/neomycin sulfate/hydrocortisone acetate/thonzonium bromide (commercially available as Cortisporin-TC Otic®), cephalexin hydrochloride (commercially available as Keflex®), cefdinir (commercially available as Omnicef®), and gatifloxacin (commercially available as Zymar®).

Other useful actives include cancer treatment medications, including cyclophosphamide (commercially available as Cytoxan®), methotrexate (commercially available as Rheumatrex® and Trexal®), tamoxifen citrate (commercially available as Nolvadex®), bevacizumab (commercially available as Avastin®), everolimus (commercially available as Afinitor®), pazopanib (commercially available as Votrient®), and anastrozole (commercially available as Arimidex®); leukemia treatment, such as ofatumumab (commercially available as Arzerra®); anti-thrombotic drugs, such as antithrombin recombinant lyophilized powder (commercially available as Atryn®), prasugrel (commercially available as Efient®); anti-coagulants, such as aspirin with extended-release dipyridamole (commercially available as Aggrenox®), warfarin sodium (commercially available as Coumadin®), dipyridamole (commercially available as Persantine®), dalteparin (commercially available as Fragmin®), danaparoid (commercially available as Orgaran®), enoxaparin (commercially available as Lovenox®), heparin (commercially available as Hep-Lock, Hep-Pak, Hep-Pak CVC, Heparin Lock Flush), tinzaparin (commercially available as Innohep®), and clopidogrel bisulfate (commercially available as Plavix®); antiemetics, such as granisetron hydrochloride (commercially available as Kytril®) and nabilone (commercially available as Cesamet®), trimethobenzamide hydrochloride (commercially available as Tigan®), and ondansetron hydrochloride (commercially available as Zofran®); anti-fungal treatment, such as ketoconazole (commercially available as Nizoral®), posaconazole (commercially available as Noxafil®), ciclopirox (commercially available as Penlac®), griseofulvin (commercially available as Gris-PEG®), oxiconazole nitrate (commercially available as Oxistat®), fluconazole (commercially available as Diflucan®), sertaconazole nitrate (commercially available as Ertaczo®), terbinafine hydrochloride (commercially available as Lamisil®), ciclopirox (commercially available as Loprox®), nystatin/triamcinolone acetonide (commercially available as Mycolog-II®), econazole nitrate (commercially available as Spectazole®), itraconazole (commercially available as Sporanox®), and terconazole (commercially available as Terazol®).

Active agents may further include anti-inflammatory medications, such as hydroxychloroquine sulfate (commercially available as Plaquenil®), fluticasone propionate (commercially available as Cutivate®), canakinumab (commercially available as Llaris®), amcinonide (commercially available as Cyclocort®), methylprednisolone (commercially available as Medrol®), budesonide (commercially available as Entocort EC®), anakinra (commercially available as Kineret®), diflorasone diacetate (commercially available as Psorcon®), and etanercept (commercially available as Enbrel®); antispasmodic medication, such as phenobarbital/hyoscyamine sulfate/atropine sulfate/scopolamine hydrobromide (commercially available as Donnatal®); antiviral treatment, such as oseltamivir phosphate (commercially available as Tamiflu®); anti-parasites medication, including tinidazole (commercially available as Tindamax®); appetite treatment mediations, such as megestrol acetate (commercially available as Megace ES®), phentermine hydrochloride (commercially available as Adipex-P®), and diethylpropion hydrochloride (commercially available as Tenuate®); arthritis medications, including leflunomide (commercially available as Arava®), certolizumab pegol (commercially available as Cimzia®), diclofenac sodium (commercially available as Pennsaid®), golimumab (commercially available as Simponi®), and tocilizumab (commercially available as Actemra®); bladder control medication, such as trospium chloride (commercially available as Sanctura®), desmopressin acetate (commercially available as DDAVP®), tolterodine tartrate (commercially available as Detrol®), oxybutynin chloride (commercially available as Ditropan® or Gelnique®), darifenacin (commercially available as Enablex®), and solifenacin succinate (commercially available as VESIcare®); blood vessel constrictors, such as methylergonovine maleate (commercially available as Methergine®); plasma uric managers, such as rasburicase (commercially available as Elitek®); iron deficiency anemia medications, such as ferumoxytol (commercially available as Feraheme®); lymphoma medications, such as pralatrexate (commercially available as Folotyn®), romidepsin (commercially available as Isodax®); malaria medication, such as artemether/lumefantrine (commercially available as Coartem®); hyponatremia medication, such as tolvatpan (commercially available as Samsca®); medication for treatment of von Willebrand disease (commercially available as Wilate®); anti-hypertension medications, such as treprostinil (commercially available as Tyvaso®), tadalafil (commercially available as Adcirca®); cholesterol lowering medication, including paricalcitol (commercially available as Altocor®), pitavastatin (commercially available as Livalo®), lovastatin, niacin (commercially available as Advicor®), colestipol hydrochloride (commercially available as Colestid®), rosuvastatin calcium (commercially available as Crestor®), fluvastatin sodium (commercially available as Lescol®), atorvastatin calcium (commercially available as Lipitor®), lovastatin (commercially available as Mevacor®), niacin (commercially available as Niaspan®), pravastatin sodium (commercially available as Pravachol®), pavastatin sodium with buffered aspirin (commercially available as Pravigard PAC®), cholestyramine (commercially available as Questran®), simvastatin and niacin (commercially available as Simcor®), atenolol, chlorthalidone (commercially available as Tenoretic®), atenolol (commercially available as Tenormin®), fenofibrate (commercially available as Tricor®), fenofibrate (commercially available as Triglide®), ezetimibe/simvastatin (commercially available as Vytorin®), colesevelam (commercially available as WelChol®), bisoprolol fumarate (commercially available as Zebeta®), ezetimibe (commercially available as Zetia®), bisoprolol fumarate/hydrochlorothiazide (commercially available as Ziac®), and simvastatin (commercially available as Zocor®).

The actives included herein may also include chronic kidney disease medication, such as paricalcitol (commercially available as Zemplar®); contraceptive agents, including etonogestrel (commercially available as Implanon®), norethindrone acetate, ethinyl estradiol (commercially available as Loestrin 24 FE®), ethinyl estradiol, norelgestromin (commercially available as Ortho Evra®), levonorgestrel (commercially available as Plan B®), levonorgestrel and ethinyl estradiol (commercially available as Preven®), levonorgestrel, ethinyl estradiol (commercially available as Seasonique®), and medroxyprogesterone acetate (commercially available as Depo-Provera®); COPD medication, such as arformoterol tartrate (commercially available as Brovana®) and ipratropium bromide, albuterol sulfate (commercially available as Combivent®); cough suppressants, including benzonatate (commercially available as Tessalon®), guaifenesin, codeine phosphate (commercially available as Tussi-Organidin NR®), and acetaminophen, codeine phosphate (commercially available as Tylenol with Codeine®); medication for the treatment of diabetes, including pioglitazone hydrochloride, metformin hydrochloride (commercially available as ACTOplus Met®), bromocriptine mesylate (commercially available as Cycloset®), liraglutide (commercially available as Victoza®), saxagliptin (commercially available as Onglyza®), pioglitazone hydrochloride (commercially available as Actos®), glimepiride (commercially available as Amaryl®), rosiglitazone maleate, metformin hydrochloride (commercially available as Avandamet®), rosiglitazone maleate (commercially available as Avandaryl®), rosiglitazone maleate (commercially available as Avandia®), exenatide (commercially available as Byetta®), chlorpropamide (commercially available as Diabinese®), pioglitazone hydrochloride, glimepiride (commercially available as Duetact®), metformin hydrochloride (commercially available as Glucophage®), glipizide (commercially available as Glucotrol®), glyburide, metformin (commercially available as Glucovance®), metformin hydrochloride (commercially available as Glumetza®), sitagliptin (commercially available as Januvia®), detemir (commercially available as Levemir®), glipizide, metformin hydrochloride (commercially available as Metaglip®), glyburide (commercially available as Micronase®), repaglinide (commercially available as Prandin®), acarbose (commercially available as Precose®), nateglinide (commercially available as Starlix®), pramlintide acetate (commercially available as Symlin®), and tolazamide (commercially available as Tolinase®).

Other useful agents of the present invention may include digestive agents, such as sulfasalazine (commercially available as Azulfidine®), rabeprazole sodium (commercially available as AcipHex®), lubiprostone (commercially available as Amitiza®), dicyclomine hydrochloride (commercially available as Bentyl®), sucralfate (commercially available as Carafate®), lactulose (commercially available as Chronulac®), docusate (commercially available as Colace®), balsalazide disodium (commercially available as Colazal®), losartan potassium (commercially available as Cozaar®), olsalazine sodium (commercially available as Dipentum®), chlordiazepoxide hydrochloride, clidinium bromide (commercially available as Librax®), esomeprazole magnesium (commercially available as Nexium®), famotidine (commercially available as Pepcid®), lansoprazole (commercially available as Prevacid®), lansoprazole and naproxen (commercially available as Prevacid NapraPAC®), amoxicillin/clarithromycin/lansoprazole (commercially available as Prevpac®), omeprazole (commercially available as Prilosec®), pantoprazole sodium (commercially available as Protonix®), metoclopramide hydrochloride (commercially available as Reglan® or Metozolv®), cimetidine (commercially available as Tagamet®), ranitidine hydrochloride (commercially available as Zantac®), and omeprazole, sodium bicarbonate (commercially available as Zegerid®); diuretics, including spironolactone, hydrochlorothiazide (commercially available as Aldactazide®), spironolactone (commercially available as Aldactone®). bumetanide (commercially available as Bumex®), torsemide (commercially available as Demadex®), chlorothiazide (commercially available as Diuril®), furosemide (commercially available as Lasix®), metolazone (commercially available as Zaroxolyn®), and hydrochlorothiazide, triamterene (commercially available as Dyazide®).

Agents useful herein may also include treatment for emphysema, such as tiotropium bromide (commercially available as Spiriva®); fibromyalgia medication, such as milnacipran hydrochloride (commercially available as Savella®); medication for the treatment of gout, such as colchicine (commercially available as Colcrys®), and febuxostat (commercially available as Uloric®); enema treatments, including aminosalicylic acid (commercially available as Mesalamine® and Rowasa®); epilepsy medications, including valproic acid (commercially available as Depakene®), felbamate (commercially available as Felbatol®), lamotrigine (commercially available as Lamictal®), primidone (commercially available as Mysoline®), oxcarbazepine (commercially available as Trileptal®), zonisamide (commercially available as Zonegran®), levetiracetam (commercially available as Keppra®), and phenytoin sodium (commercially available as Dilantin®).

Erectile dysfunction therapies useful herein include, but are not limited to, drugs for facilitating blood flow to the penis, and for effecting autonomic nervous activities, such as increasing parasympathetic (cholinergic) and decreasing sympathetic (adrenersic) activities. Useful agents for treatment of erectile dysfunction include, for example, those agents available as alprostadil (commercially available as Caverject®), tadalafil (commercially available as Cialis®), vardenafil (commercially available as Levitra®), apomorphine (commercially available as Uprima®), yohimbine hydrochloride (commercially available as Aphrodyne®, Yocon®), and sildenafil citrate (commercially available as Viagra®).

Agents useful herein may further include eye medications and treatment, such as dipivefrin hydrochloride (commercially available as Propine®), valganciclovir (commercially available as Valcyte®), ganciclovir ophthalmic gel (commercially available as Zirgan®); bepotastine besilate (commercially available as Bepreve®), besifloxacin (commercially available as Besivance®), bromfenac (commercially available as Xibrom®), fluorometholone (commercially available as FML®), pilocarpine hydrochloride (commercially available as Pilocar®), cyclosporine (commercially available as Restasis®), brimonidine tartrate (commercially available as Alphagan P®), dorzolamide hydrochloride/timolol maleate (commercially available as Cosopt®), bimatoprost (commercially available as Lumigan®), timolol maleate (available as Timoptic®), travoprost (commercially available as Travatan®), latanoprost (commercially available as Xalatan®), echothiophate iodide (commercially available as Phospholine Iodide®), and ranibizumab (commercially available as Lucentis®); fluid controllers, such as acetazolamide (commercially available as Diamox®); gallstone medications, including ursodiol (commercially available as Actigall®); medication for the treatment of gingivitis, including chlorhexidine gluconate (commercially available as Peridex®); headache medications, including butalbital/codeine phosphate/aspirin/caffeine (commercially available as Fiornal® with Codeine), naratriptan hydrochloride (commercially available as Amerge®), almotriptan (commercially available as Axert®), ergotamine tartrate/caffeine (commercially available as Cafergot®), butalbital/acetaminophen/caffeine (commercially available as Fioricet®), butalbital/aspirin/caffeine (commercially available as Fiorinal®), frovatriptan succinate (commercially available as Frova®), rizatriptan benzoate (commercially available as Maxalt®), isometheptene mucate/dichloralphenazone/acetaminophen (commercially available as Midrin®), dihydroergotamine mesylate (commercially available as Migranal®), eletriptan hydrobromide (commercially available as Relpax®), and zolmitriptan (commercially available as Zomig®); influenza medication, such as haemophilus b conjugate vaccine; tetanus toxoid conjugate (commercially available as Hiberix®); and heart treatments, including quinidine sulfate, isosorbide dinitrate/hydralazine hydrochloride (commercially available as BiDil®), digoxin (commercially available as Lanoxin®), flecainide acetate (commercially available as Tambocor®), mexiletine hydrochloride (commercially available as Mexitil®), disopyramide phosphate (commercially available as Norpace®), procainamide hydrochloride (commercially available as Procanbid®), and propafenone (commercially available as Rythmol®).

Other useful agents include hepatitis treatments, including entecavir (commercially available as Baraclude®), hepatitis B immune globulin (commercially available as HepaGam B®), and copegus/rebetol/ribasphere/vilona/virazole (commercially available as Ribavirin®); herpes treatments, including valacyclovir hydrochloride (commercially available as Valtrex®), penciclovir (commercially available as Denavir®), acyclovir (commercially available as Zovirax®), and famciclovir (commercially available as Famvir®); treatment for high blood pressure, including enalaprilat (available as Vasotec®), captopril (available as Capoten®) and lisinopril (available as Zestril®), verapamil hydrochloride (available as Calan®), ramipril (commercially available as Altace®), olmesartan medoxomil (commercially available as Benicar®), amlodipine/atorvastatin (commercially available as Caduet®), nicardipine hydrochloride (commercially available as Cardene®), diltiazem hydrochloride (commercially available as Cardizem®), quinapril hydrochloride (commercially available as Accupril®), quinapril hydrochloride/hydrochlorothiazide (commercially available as Accuretic®), perindopril erbumine (commercially available as Aceon®), candesartan cilexetil (commercially available as Atacand®), candesartan cilexetil/hydrochlorothiazide (commercially available as Atacand HCT®), irbesartan/hydrochlorothiazide (commercially available as Avalide®), irbesartan (commercially available as Avapro®), amlodipine besylate/olmesartan medoxomil (commercially available as Azor®), levobunolol hydrochloride (commercially available as Betagan®), betaxolol hydrochloride (commercially available as Betoptic®), nebivolol (commercially available as Bystolic®), captopril/hydrochlorothiazide (commercially available as Capozide®), doxazosin mesylate (commercially available as Cardura®), clonidine hydrochloride (commercially available as Catapres®), carvedilol (commercially available as Coreg®), nadolol (commercially available as Corgard®), nadolol/bendroflumethiazide (commercially available as Corzide®), valsartan (commercially available as Diovan®), isradipine (commercially available as DynaCirc®), Guanabenz acetate. (commercially available as Wytensin®), Guanfacine hydrochloride (commercially available as Tenex® or Intuniv®), losartan potassium/hydrochlorothiazide (commercially available as Hyzaar®), propranolol hydrochloride (commercially available as Indera®), propranolol hydrochloride/hydrochlorothiazide (commercially available as Inderide®), eplerenone (commercially available as Inspra®), ambrisentan (commercially available as Letairis®), enalapril maleate/felodipine (commercially available as Lexxel®), metoprolol tartrate (commercially available as Lopressor®), benazepril hydrochloride (commercially available as Lotensin®), benazepril hydrochloride/hydrochlorothiazide (commercially available as Lotensin HCT®), amlodipine/benazepril hydrochloride (commercially available as Lotrel®), indapamide (commercially available as Lozol®), trandolapril (commercially available as Mavik®), telmisartan (commercially available as Micardis®), telmisartan/hydrochlorothiazide (commercially available as Micardis HCT®), prazosin hydrochloride (commercially available as Minipress®), amiloride, hydrochlorothiazide (commercially available as Moduretic®), fosinopril sodium (commercially available as ZZXT Monopril®), fosinopril sodium/hydrochlorothiazide (commercially available as Monopril-HCT®), pindolol (commercially available as Visken®), felodipine (commercially available as Plendil®), sildenafil citrate (commercially available as Revatio®), Nisoldipine (commercially available as Sular®), trandolapril/verapamil hydrochloride (commercially available as Tarka®), aliskiren (commercially available as Tekturna®), eprosartan mesylate (commercially available as Teveten®), eprosartan mesylate/hydrochlorothiazide (commercially available as Teveten HCT®), moexipril hydrochloride/hydrochlorothiazide (commercially available as Uniretic®), moexipril hydrochloride (commercially available as Univasc®), enalapril maleate/hydrochlorothiazide (commercially available as Vaseretic®), and lisinopril/hydrochlorothiazide (commercially available as Zestoretic®).

The present invention may include agents useful in the medication for the treatment of HIV/AIDS, such as amprenavir (commercially available as Agenerase®), tipranavir (commercially available as Aptivus®), efavirenz/emtricitabine/tenofovir (commercially available as Atripla®), lamivudine/zidovudine (commercially available as Combivir®), indinavir sulfate (commercially available as Crixivan®), lamivudine (commercially available as Epivir®), saquinavir (commercially available as Fortovase®), zalcitabine (commercially available as Hivid®), lopinavir/ritonavir (commercially available as Kaletra®), fosamprenavir calcium (commercially available as Lexiva®), ritonavir (commercially available as Norvir®), zidovudine (commercially available as Retrovir®), atazanavir sulfate (commercially available as Reyataz®), efavirenz (commercially available as Sustiva®), abacavir/lamivudine/zidovudine (commercially available as Trizivir®), didanosine (commercially available as Videx®), nelfinavir mesylate (commercially available as Viracept®), nevirapine (commercially available as Viramune®), tenofovir disoproxil fumarate (commercially available as Viread®), stavudine (commercially available as Zerit®), and abacavir sulfate (commercially available as Ziagen®); homocysteiene removers, including betaine anhydrous (commercially available as Cystadane®); medications, such as insulin (commercially available as Apidra®, Humalog®, Humulin®, Iletin®, and Novolin®); and HPV treatment, such as Human papillomavirus vaccine (commercially available as Gardasil®) or human papillomavirus bivalent (commercially available as Cervarix®); immunosuppressants, including cyclosporine (commercially available as Gengraf®, Neoral®, Sandimmune®, and Apo-Cyclosporine®).

Agents useful in the present invention may further include prolactin inhibitors, such as bromocriptine mesylate (commercially available as Parlodel®); medications for aiding in stress tests, such as regadenoson (commercially available as Lexiscan®); baldness medication, including finasteride (commercially available as Propecia® and Proscar®); pancreatitis treatment, such as gemfibrozil (commercially available as Lopid®); hormone medications, such as norethindrone acetate/ethinyl estradiol (commercially available as femHRT®), goserelin acetate (commercially available as Zoladex®), progesterone gel (commercially available as Prochieve®), progesterone (commercially available as Prometrium®), calcitonin-salmon (commercially available as Miacalcin®), calcitriol (commercially available as Rocaltrol®), Synthroid (commercially available as Levothroid®, Levoxyl®, Unithroid®), testosterone (commercially available as Testopel®, Androderm®, Testoderm®, and AndroGel®); menopause medication, such as estradiol/norethindrone acetate (commercially available as Activella®), drospirenone/estradiol (commercially available as Angeliq®), estradiol/levonorgestrel (commercially available as Climara Pro®), estradiol/norethindrone acetate (commercially available as CombiPatch®), estradiol (commercially available as Estrasorb®, Vagifem® and EstroGel®), esterified estrogens and methyltestosterone (commercially available as Estratest®), estrogen (commercially available as Alora®, Climara®, Esclim®, Estraderm®, Vivelle®, Vivelle-Dot®), estropipate (commercially available as Ogen®), conjugated estrogens (commercially available as Premarin®), and medroxyprogesterone acetate (commercially available as Provera®); menstrual medications, including leuprolide acetate (commercially available as Lupron Depot), tranexamic acid (commercially available as Lysteda®), and norethindrone acetate (commercially available as Aygestin®); and muscle relaxants, including cyclobenzaprine hydrochloride (commercially available as Flexeril®), tizanidine (commercially available as Zanaflex®), and hyoscyamine sulfate (commercially available as Levsin®).

Agents useful herein may also include osteoporosis medications, including ibrandronate sodium (commercially available as Boniva®), risedronate (commercially available as Actonel®), raloxifene hydrochloride (commercially available as Evista®, Fortical®), and alendronate sodium (commercially available as Fosamax®); ovulation enhancers, including clomiphene citrate (commercially available as Serophene®, Clomid®, Serophene®); Paget's disease treatment, such as etidronate disodium (commercially available as Didronel®); pancreatic enzyme deficiency medications, such as pancrelipase (commercially available as Pancrease® or Zenpep®); medication for the treatment of Parkinson's disease, such as pramipexole dihydrochloride (commercially available as Mirapex®), ropinirole hydrochloride (commercially available as Requip®), carbidopa/levodopa (commercially available as Sinemet CRC), carbidopa/levodopa/entacapone (commercially available as Stalevo®), selegiline hydrochloride (commercially available as Zelapar®), rasagiline (commercially available as Azilect®), entacapone (commercially available as Comtan®), and selegiline hydrochloride (commercially available as Eldepryl®); multiple sclerosis medication, such as dalfampridine (commercially available as Ampyra®) and interferon beta-1 b (commercially available as Extavia®); prostate medication, including flutamide (commercially available as Eulexin®), nilutamide (commercially available as Nilandron®), dutasteride (commercially available as Avodart®), tamsulosin hydrochloride (commercially available as Flomax®), terazosin hydrochloride (commercially available as Hytrin®), and alfuzosin hydrochloride (commercially available as UroXatral®).

Films of the present invention may further include psychiatric medications, including alprazolam (available as Niravam®, Xanax®), clozopin (available as Clozaril®), haloperidol (available as Haldol®), fluoxetine hydrochloride (available as Prozac®), sertraline hydrochloride (available as Zoloft®), asenapine (commercially available as Saphris®), iloperidone (commercially available as Fanapt®), paroxtine hydrochloride (available as Paxil®), aripiprazole (commercially aavialbe as Abilify®), guanfacine (commercially available as Intuniv®), amphetamines and methamphetamines (commercially available as Adderall® and Desoxyn®), clomipramine hydrochloride (commercially available as Anafranil®), Buspirone hydrochloride (commercially available as BuSpar®), citalopram hydrobromide (commercially available as Celexa®), duloxetine hydrochloride (commercially available as Cymbalta®), methylphenidate (commercially available as Ritalin, Daytrana®), divalproex sodium (Valproic acid) (commercially available as Depakote®), dextroamphetamine sulfate (commercially available as Dexedrine®), venlafaxine hydrochloride (commercially available as Effexor®), selegiline (commercially available as Emsam®), carbamazepine (commercially available as Equetro®), lithium carbonate (commercially available as Eskalith®), fluvoxamine maleate/dexmethylphenidate hydrochloride (commercially available as Focalin®), ziprasidone hydrochloride (commercially available as Geodon®), ergoloid mesylates (commercially available as Hydergine®), escitalopram oxalate (commercially available as Lexapro®), chlordiazepoxide (commercially available as Librium®), molindone hydrochloride (commercially available as Moban®), phenelzine sulfate (commercially available as Nardil®), thiothixene (commercially available as Navane®), desipramine hydrochloride (commercially available as Norpramin®), benzodiazepines (such as those available as Oxazepam®), nortriptyline hydrochloride (commercially available as Pamelor®), tranylcypromine sulfate (commercially available as Parnate®), prochlorperazine, mirtazapine (commercially available as Remeron®), risperidone (commercially available as Risperdal®), quetiapine fumarate (commercially available as Seroquel®), doxepin hydrochloride (commercially available as Sinequan®), atomoxetine hydrochloride (commercially available as Strattera®), trimipramine maleate (commercially available as Surmontil®), olanzapine/fluoxetine hydrochloride (commercially available as Symbyax®), imipramine hydrochloride (commercially available as Tofranil®), protriptyline hydrochloride (commercially available as Vivactil®), bupropion hydrochloride (commercially available as Wellbutrin®, Wellbutrin SR®), and Wellbutrin XR®), and olanzapine (commercially available as Zyprexa®).

Agents useful herein may also include uric acid reduction treatment, including allopurinol (commercially available as Zyloprim®); seizure medications, including gabapentin (commercially available as Neurontin®), ethotoin (commercially available as Peganone®), vigabatrin (commercially available as Sabril®), and topiramate (commercially available as Topamax®); treatment for shingles, such as zoster vaccine live (commercially available as Zostavax®); skin care medications, including calcipotriene (commercially available as Dovonex®), ustekinumab (commercially available as Stelara®), televancin (commercially available as Vibativ®), isotretinoin (commercially available as Accutane®), hydrocortisone/iodoquinol (commercially available as Alcortin®), sulfacetamide sodium/sulfur (commercially available as Avar®), azelaic acid (commercially available as Azelex®, Finacea®), benzoyl peroxide (commercially available as Desquam-E®), adapalene (commercially available as Differin®), fluorouracil (commercially available as Efudex®), pimecrolimus (commercially available as Elidel®), topical erythromycin (commercially available as A/T/S®, Erycette®, T-Stat®), hydrocortisone (commercially available as Cetacort®, Hytone®, Nutracort®), metronidazole (commercially available as MetroGel®), doxycycline (commercially available as Oracea®), tretinoin (commercially available as Retin-A® and Renova®), mequinol/tretinoin (commercially available as Solage®), acitretin (commercially available as Soriatane®), calcipotriene hydrate/betamethasone dipropionate (commercially available as Taclonex®), tazarotene (commercially available as Tazorac®), fluocinonide (commercially available as Vanos®), desonide (commercially available as Verdeso®), miconazole nitrate/Zinc oxide (commercially available as Vusion®), ketoconazole (commercially available as Xolegel®), and efalizumab (commercially available as Raptiva®).

Other agents useful herein may include sleep disorder medications, including zaleplon (available as Sonata®), eszopiclone (available as Lunesta®), zolpidem tartrate (commercially available as Ambient, Ambien CR®, Edluar®), lorazepam (commercially available as Ativan®), flurazepam hydrochloride (commercially available as Dalmane®), triazolam (commercially available as Halcion®), clonazepam (commercially available as Klonopin®), barbituates, such as Phenobarbital®), Modafinil (commercially available as Provigil®), temazepam (commercially available as Restoril®), ramelteon (commercially available as Rozerem®), clorazepate dipotassium (commercially available as Tranxene®), diazepam (commercially available as Valium®), quazepam (commercially available as Doral®), and estazolam (commercially available as ProSom®); smoking cessation medications, such as varenicline (commercially available as Chantix®), nicotine, such as Nicotrol®, and bupropion hydrochloride (commercially available as Zyban®); and steroids, including alclometasone dipropionate (commercially available as Aclovate®), betamethasone dipropionate (commercially available as Diprolene®), mometasone furoate (commercially available as Elocon®), fluticasone (commercially available as Flonase®, Flovent®, Flovent Diskus®, Flovent Rotadisk®), fluocinonide (commercially available as Lidex®), mometasone furoate monohydrate (commercially available as Nasonex®), desoximetasone (commercially available as Topicort®), clotrimazole/betamethasone dipropionate (commercially available as Lotrisone®), prednisolone acetate (commercially available as Pred Forte®, Prednisone®, Budesonide Pulmicort®, Rhinocort Aqua®), prednisolone sodium phosphate (commercially available as Pediapred®), desonide (commercially available as Tridesilon®), and halobetasol propionate (commercially available as Ultravate®).

Films of the present invention may further include agents useful for thyroid disease treatment, such as hormones TC and TD (commercially available as Armour Thyroid®); potassium deficiency treatment, including potassium chloride (commercially available as Micro-K®); triglycerides regulators, including omega-3-acid ethyl esters (commercially available as Omacor®); urinary medication, such as phenazopyridine hydrochloride (commercially available as Pyridium®) and methenamine, methylene blue/phenyl salicylate/benzoic acid/atropine sulfate/hyoscyamine (commercially available as Urised®); prenatal vitamins (commercially available as Advanced Natalcare®, Materna®, Natalins®, Prenate Advance®); weight control medication, including orlistat (commercially available as Xenical®) and sibutramine hydrochloride (commercially available as Meridia®).

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

In one particular method of forming a film, a wet film matrix is deposited onto the surface of a substrate. Any desired substrate may be used, including, for example, mylar, paper, plastic, metal, foil, and combinations thereof. The substrate may be laminated if desired. Further, the substrate may be chemically treated on one or more surfaces prior to depositing the wet film matrix thereon. Desirably, the substrate is substantially flat, but is flexible to allow for rolling, such as for storage or for packaging of the formed film products. The substrate may include one or more dams, such as that disclosed in Applicant's co-pending U.S. patent application Ser. No. 12/711,883, filed Feb. 24, 2010, the entire contents of which are incorporated by reference herein. In some embodiments, the substrate may include a pre-formed sheet of dissolvable and/or ingestible film, where the wet film-forming matrix is deposited onto the sheet, providing a multi-layered film product. In still other embodiments, the substrate may include a plurality of pre-formed film products on its surface, and the wet film matrix is deposited onto the surface of the pre-formed film products.

The substrate may have any length and width desired, depending on the size of the apparatus used to process the film. The length of the substrate is not critical, since the substrate may generally be fed into the film-forming apparatus on a continuous basis and sized by the user accordingly. The width of the substrate is sized to be fed into the apparatus used, and may vary as desired. The width of the substrate typically determines the width of the film product that can be prepared on that substrate. For example, a plurality of film strips or individual film products may be prepared on the substrate, arranged in a substantially side-by-side manner, and the cumulative width of those film strips or products dictates the desired width of the substrate. It is typical then that the batch size determines the cumulative width of the film, which in turn determines the optimum width of the substrate. The width of the individual film strips or products may be relatively small, for example, ranging from about 2 mm to about 30 mm. The width of individual film strips may be from about 2 mm to about 10 mm, or from about 10 mm to about 20 mm. It may, in some instances, be desired that the individual film strips include a width that is greater than 30 mm. It should be understood that the "width of the individual film strips" is intended to be an average width, and there may be some variation between individual film strips formed via the present invention.

There may be deposited on the substrate any number of individual film strips or products. In some embodiments, there may be deposited between about 2 to about 30 individual film strips or products on a substrate, the film strips or products arranged in a substantially side-by-side fashion with a gap separating adjacent film strips. In some embodiments, there may be between about 10 to about 20 individual film strips or products on a substrate. It may be desired, for example, during a test run or other experimental procedure, that only one film strip or product be deposited on the substrate. Desirably, the width of the substrate is at least 1 inch wider than the cumulative width of the dried film strips or products and any gaps therebetween. Having a substrate wider than the cumulative width of the dried film strips or products and gaps therebetween is useful in processing the product(s), as it allows some tolerance during the process.

In use, a wet film-forming matrix is deposited onto the top surface of the substrate, as will be described in further detail below. In a preferred embodiment, the wet matrix is deposited onto the substrate via extrusion, however, the wet matrix may be deposited onto the substrate via any means desired, including coating, casting, spraying, or other means. The wet matrix may be deposited in one continuous strip or stripe, which results in a dried film stripe, and which is then capable of being cut into several smaller individual dosages. Alternatively, the wet matrix may be deposited in discrete amounts, such that the deposited wet matrix has a width and length that is capable of being dried to form an individual film product having the desired width and length.

Once deposited on the surface of the substrate, the deposited wet matrix may be dried through any desired drying means, including but not limited to those methods set forth in the patents and applications previously incorporated by reference above. For example, the film matrix may be rapidly dried in an oven so as to provide a viscoelastic mass within the first about 0.5 to about 4.0 minutes, thus "locking in" the components of the film forming matrix. The resulting viscoelastic mass may then be further dried to provide the final film product. One benefit of drying a film product on the surface of a substrate is that the film may be dried quickly and efficiently, resulting in a film that has a substantially flat form. Further, the film may become adhered to the surface of the substrate during drying, which aids in packaging and dispensing the end product. If desired, the resulting dried film product and the substrate upon which it has been deposited may be die cut and packaged together, thereby minimizing the requirement to remove the film product from the substrate prior to packaging. It may be desirable, for example, for the film product to remain adhered to the substrate, and the film product/substrate product be provided to an end user. For example, the present method may be useful in forming a continuous stripe of film product, which may be rolled and dispensed through an apparatus such as that described in Applicant's co-pending application, U.S. patent application Ser. No. 12/711,899, filed on Feb. 24, 2010, entitled "Device And System For Determining, Preparing And Administering Therapeutically Effective Doses", the entire contents of which are incorporated herein by reference.

With reference to the Figures, the present invention provides a system and method for efficiently and continuously producing film products, especially individual film products or film stripes, with minimal waste. The film products formed through the present invention provide high content uniformity and therefore provide film products having highly accurate dosages. In one embodiment set forth in FIG. 1, a film forming apparatus 10 is provided. The film forming apparatus 10 includes a substrate 20. As explained above, the substrate may be formed from any desired materials, including, for example, mylar, paper, plastic, metal, foil, and combinations thereof. The substrate 20 may be laminated if desired. Further, the substrate 20 may be chemically treated prior to depositing a wet film matrix thereon. Desirably, the substrate 20 is substantially flat, but is flexible to allow for rolling.

In some embodiments, the substrate 20 may include a pre-formed sheet of film (such as an ingestible film or other biocompatible film product that may be applied to one or more body surfaces). The pre-formed sheet of film may be self-supporting and fed through the apparatus, or it may be pre-formed onto another substrate, whereby both are fed through the apparatus. The substrate 20 includes a top surface and a bottom surface (not shown). In this embodiment, a wet film matrix is capable of being deposited onto the top surface of the substrate 20. In embodiments where the substrate 20 is a pre-formed sheet of film, the deposition of a wet film forming matrix thereon provides a multi-layered film product, where the pre-formed film is a first layer (or "backing layer"), and the deposited film forming matrix forms a second layer (or "active layer"). It may be useful that the first layer not include an active, while the second layer includes an active, although both layers may include an active. The resulting multi-layered film may then be sized and cut to provide individual multi-layered film products.

In still other embodiments, the substrate 20 may be a sheet of a non-ingestible product (i.e., paper, mylar, etc.), which includes on its top surface a plurality of pre-formed ingestible film products formed thereon. In this embodiment, a wet film matrix may be deposited onto the top surface of the pre-formed film products. This embodiment forms a multi-layered film product without the need for further sizing or cutting the multi-layered film products. In further embodiments, described in further detail below, the apparatus 10 may include a means for forming a first layer of film product on the top surface of the substrate 20 prior to depositing a second layer (or layers) of film product onto the deposited first layer of film product.

The substrate 20 may be stored as a continuous roll of substrate 20 prior to use. In use, the first end (not shown) of the substrate 20 is fed into the apparatus 10 in the direction designated by arrow A. During use, the substrate 20 may continuously travel in the direction A, during which time a wet film matrix is deposited onto the top surface of substrate 20, and led along the direction A during the drying process, as will be described in further detail below. The substrate 20 may travel at any desired rate of speed. The rate at which the substrate 20 travels may be altered as necessary to suit the drying needs of the film-forming material in view of the desired oven temperature. For example, if a longer drying time is desired, the substrate 20 may travel at a slower rate of speed through the apparatus 10. If a shorter drying time is required, the substrate 20 may travel at a higher rate of speed through the apparatus 10. In addition, in some embodiments, the rate of speed may control the thickness of the wet film products deposited thereon. For example, in an extrusion process, a faster rate of speed of the substrate 20 may result in a thinner wet film product deposited thereon, and vice versa.

The substrate 20 may be any desired length or width, as explained above. Desirably, the width of the substrate 20 is sufficient to allow the deposition of a plurality of individual film products arranged in a substantially side-by-side pattern. For example, the substrate 20 may be wide enough to allow deposition of between about 2 to about 30 individual film products, arranged substantially side-by-side. The individual film products may have a gap between adjacent film strips, so as to allow for easier processing and distribution.

The apparatus 10 includes a reservoir 30, designed to house a predetermined amount of film forming matrix. The film forming matrix includes any desired film forming components, including, for example, polymers, solvents, sweeteners, active agents, fillers, and the like. Useful components for a film forming matrix include those disclosed in U.S. Publication No. 2005/0037055, the contents of which are incorporated by reference herein in entirety. The reservoir 30 may include more than one separate housings or compartments to store the various components of the film forming matrix. For example, it may be desired to store the active component in a separate container than solvents or polymers until immediately prior to deposition onto the substrate 20. The reservoir 30 is preferably pressurized, such that it may effectively force the film forming matrix housed therein through the apparatus 10.

In some embodiments, the apparatus 10 is capable of extruding a film forming matrix, as will be explained in further detail below. In such embodiments, it may be desired that the film forming matrix have a high viscosity and/or a high solids content. For example, the film forming matrix may include at least 30% solids content, or it may include at least 25% solids content, or alternatively, it may include at least 20% solids content. In other embodiments, the matrix may be a slurry or suspension of solids in a fluid carrier. The apparatus 10 and methods described herein allow for processing of such a film forming matrix having a high solid content without fear of clogs or blockages in the system. Alternatively, the film forming matrix may have a low solid content, and may have a lower viscosity, if desired. It is preferable that the film-forming matrix have a sufficient viscosity so as to generally maintain its shape upon disposition onto the surface of the substrate 20.

Attached to the reservoir 30 is a feed line or tube 40, which is in fluid connection with the reservoir 30 and connects the reservoir 30 to a plurality of volumetric pumps 50, 50'. The feed line 40 may be made of any desired material, and may have any thickness or radius desired. It is preferable that the feed line 40 have a sufficient radius so as to effectively transport the film forming matrix from the reservoir 30 to the volumetric pumps 50 without blockage, clogging, or exhibiting a sufficient pressure drop as to insufficiently supply material to the pumps. The apparatus 10 may include any number of volumetric pumps 50 desired, depending upon the number of individual film products that the user wishes to produce. In one embodiment, each volumetric pump 50 in the apparatus 10 will be used to form film products, and thus the number of volumetric pumps 50 used may dictate the number of film products formed. The volumetric pumps 50 are desirably arranged in a side-by-side pattern in the apparatus 10. The feed line 40 desirably feeds the film forming matrix from the reservoir 30 to the volumetric pumps 50 in a parallel fashion, thus allowing each volumetric pump 50 to be fed with the film forming matrix on a substantially equal basis.

The volumetric pumps 50 may be any type of pumping apparatus desired by the user. Desirably, the volumetric pumps 50 are each of approximately equal size and shape, and are capable of dispensing substantially the same amount of film forming matrix therefrom. It is particularly desired to use a pump 50 that is capable of dispensing a known amount of matrix per each pumping cycle. Further, the pump 50 should be capable of being re-filled with film forming matrix after a pre-determined amount of film forming matrix has been dispensed via pumping. In particular, it is desired that the pump 50 be re-filled with substantially the same amount of film-forming matrix after each pumping cycle. Thus, each pumping cycle (which includes one dispensing of film forming matrix and one re-filling of film forming matrix) should include a substantially constant amount of film forming matrix. As can be understood, regardless of the type of pump used, it is important that the pumps 50 provide an accurate and consistent dispense of the wet film matrix, so as to ensure substantial uniformity between and among each of the resulting film products.

In one embodiment, the volumetric pumps 50 are piston pumps. If desired, the volumetric pumps 50 may include dual piston pumps, where, as the pump 50 dispenses the volume of film-forming matrix, the pump 50 concurrently is re-filled with another volume of film-forming matrix. In other embodiments, the volumetric pumps 50 may include gear pumps. For formation of film-containing patches, dual piston pumps are particularly desired. The apparatus 10 may include a combination of at least one piston pump, at least one dual piston pump, at least one gear pump, and combinations thereof. Piston pumps and dual piston pumps are especially preferred, since such pumps have "suck back" capability and are thus able to prevent or reduce the amount of drool after the wet film matrix has been pumped therefrom. Further, piston pumps and dual piston pumps provide the ability to continuously load and extrude the wet film forming matrix as the substrate 20 moves. These pumps are efficient and further avoid the requirement of having a head manifold move back and forth, as in typical systems.

In some embodiments, the volumetric pumps 50 may have variable stroke and/or variable speed settings. That is, the volumetric pumps 50 may have a variable stroke, allowing the user to be able to change the stroke associated with the pump 50 to suit the particular needs. In some embodiments, the volumetric pumps 50 may dispense anywhere from about 4 microliters per stroke to about 100 microliters per stroke. Further, the volumetric pumps 50 may be variable speed pumps, to allow the user to set the particular speed desired for the particular film product being formed. For example, if a longer drying time is desired by the user, the volumetric pump 50 may be set to a slower dispensing speed, allowing for a longer process and thus a longer drying time. Alternatively, for a shorter drying time, a higher speed pump may be desired. The speed and stroke of the volumetric pumps 50 may be related to the speed at which the substrate 20 travels through the apparatus 10.

The volumetric pumps 50 used herein should be sized appropriately to provide the desired film volume. In particular, the volumetric pumps 50 should be sized to fill and dispense sufficient amount of film forming matrix to form one individual film product having the desired volume. For example, in one embodiment, the desired resultant dried individual film product may be about 1 mg to about 20 mg in total weight. In some embodiments, the dried individual film product may be 60 mg in total weight or less. It is to be understood that the weight of a wet film product will be higher than the resulting dried film product, due to loss of certain volatiles. The volumetric pumps 50 should be capable of dispensing about 3 microliters to about 250 microliters per pumping cycle, or alternatively 250 microliters or less per pumping cycle. For transdermal systems, the desired resultant individual dried film product may be about 10 mg to about 2000 mg in total weight. Thus, the volumetric pumps 50 should be capable of dispensing about 30 microliters to about 10 milliliters per pumping cycle to provide the desired resulting dried film weight.

In another embodiment, the volumetric pump 50 can be a positive displacement pump. Examples include a progressive cavity pump also known as a progressing cavity pump, eccentric screw pump or even just cavity pump. One specific example of this type of pump is the Moyno® pump (manufactured by Moyno, Inc.). Additional positive displacement pumps include gear pumps, rotary lobe pumps, piston pumps, diaphragm pumps, screw pumps, hydraulic pumps, vane pumps, regenerative (peripheral) pumps and peristaltic pumps. Systems of the present invention may include one or more than one of the aforementioned volumetric pumps 50.

Each of the volumetric pumps 50 is desirably associated with a coating head manifold 60, which includes a plurality of orifices 70, 70'. Desirably, each volumetric pump 50 is associated with one individual orifice 70. The volumetric pump 50 is in fluid communication with the orifice 70 with which it is associated, thus allowing the film forming matrix to be pumped from the pump 50 through the orifice 70. In one particular embodiment, the orifices 70 are slot dies, but the orifices 70 may be any other opening or die desired. The orifice 70 is desirably sized so as to allow the formation of the desired film product.

The orifices 70 are desirably in communication with the substrate 20, such that when a particular amount of wet film forming matrix is dispensed through the orifice 70, the wet film forming matrix is deposited onto the top surface of the substrate 20. Thus, in one embodiment, the manifold 60 has a first side 65A and a second side 65B, with the orifice 70 extending through the manifold 60 from the first side 65A to the second side 65B. The pump 50 is in communication with the first side 65A of the manifold. The wet film matrix is pumped from the reservoir 30, through feed line 40, through the pump 50, through the orifice 70, and deposited onto the substrate 20, which, during operation, is traveling in the direction A. It is particularly desirable that the wet film matrix be extruded through the orifice 70 directly onto the substrate 20, and thus the wet film matrix should have sufficiently high viscosity and/or solids content so as to allow for extrusion. In addition, the wet film forming matrix should have a sufficient viscosity so as to generally maintain its shape and size after deposition onto the surface of the substrate 20. It is contemplated, of course, that the matrix may alternatively have a lower viscosity, and that the matrix may be simply flowed through the orifice 70 onto the substrate 20. The substrate 20 may have discrete dams, wells or pockets formed therein, between or into which the wet film forming matrix may be deposited.

In one embodiment, a plurality of individual wet film products 80, 80' is deposited onto the surface of the substrate 20 in a substantially side-by-side manner. The individual wet film products 80 are deposited onto the substrate 20 as the substrate 20 moves through the apparatus 10, and preferably, each individual wet film product 80 is extruded onto a region of the substrate 20 where no individual wet film product 80 has already been extruded. Thus, the substrate 20 may have a plurality of individual wet film products 80 deposited along its length and its width. Each individual wet film product 80 is sized so as to provide the desired final dried film product. The speed at which the substrate 20 travels during the deposition of the wet film product 80 thereon may dictate or control the size of the wet film product 80. In particular, the thickness of the wet film product 80 may be controlled by the speed of the substrate 20, where a faster moving substrate 20 may provide a thinner wet film product 80, and vice versa.

During use, each pump 50 dispenses a plurality of individual wet film products 80 onto the substrate 20 in a lane (85A, 85B, 85C). Each lane (85) includes a plurality of individual wet film products 80. Desirably, each of the individual wet film products 80 has a substantially uniform size, shape, and content. In this fashion, the known dosage amount between each of the individual wet film products 80 can be known with a great deal of accuracy. The individual wet film products 80 may be deposited directly onto a non-film substrate 20, or the individual wet film products 80 may be deposited onto a substrate 20 that is a pre-formed film (thus forming a multi-layered film product). It is desired that the volumetric pumps 50 repeatedly dispense the individual wet film products 80 onto the surface of the substrate 20, so as to form the lane 85 of individual wet film products 80.

Any number of individual wet film products 80 may be deposited onto the surface of the substrate 20. The number of lanes 85 of wet film products 80 depends upon the number of pumps 50 and orifices 70 in the apparatus 10. For example, if the apparatus 10 includes five pumps 50 and orifices 70 associated therewith; there will be five lanes 85 of wet film products 80 formed on the substrate 20. Any number of pumps 50 and orifices 70 may be used in the apparatus 10, and desirably there may be between about 2 and about 30 pumps 50 and orifices 70 in the apparatus 10. Therefore, there may be between about 2 and about 30 lanes 85 of individual wet film products 80 formed on the substrate 20. Depending upon the speed and rate of the pump 50 and the substrate 20, there may be any number of individual wet film products 80 per each lane 85. As depicted in FIG. 1, there is desirably a slight gap between each individual film product 80 in the lane 85, and there is a slight gap between each adjacent lane 85. Gaps between individual wet film products 80 may aid in the processing and later packaging of the resultant film product.

As explained above, the substrate 20 may include an ingestible film product pre-formed thereon, where the wet film products 80 may be deposited directly onto the top surface of the pre-formed film product. The pre-formed film product on the substrate may be a continuous sheet of film. Alternatively, in some embodiments, the substrate 20 may have a plurality of individual film products pre-formed on the surface thereof, and the wet film matrix is deposited onto the surface of the individual film products that have been pre-formed on the substrate 20 (so as to form multi-layered film products). In this fashion, multi-layered film products may be formed with little to no cutting and sizing required, as the multi-layered individual film products may simply be removed from the substrate 20 when dried.

The individual wet film products 80 may be any shape desired, including square, rectangular, circular, or other desired shapes. The individual wet film products 80 may be any size desired, depending upon the size of the resulting dried film product desired. In some embodiments, the wet film products 80 may be small film products, i.e., being approximately 1 mg in mass each. The individual film products 80 may be larger, if desired, such as between about 1 mg and 200 mg in mass per individual film product. The individual film products 80 may be 200 mg or less, or alternatively 100 mg or less. For transdermal systems, the individual film products 80 can range from about 10 mg to about 2000 mg, or alternatively 2000 mg or less, or 1000 mg or less.

As explained above, the substrate 20 moves in the direction A during the manufacturing process. The rate of speed of the substrate 20, as well as the rate of speed of the pumps 50, determines the number of individual film products deposited onto the substrate 20 during the processing. After the individual film products 80 have been deposited onto the substrate 20, the substrate continues to move in the direction A towards a drying apparatus 90, such as an oven. The wet film products 80 may be dried via any desired manner, such as those drying methods described above. After the drying process has been complete, the plurality of dried individual film products may be removed from the substrate and packaged for distribution. Alternatively, the substrate 20 with dried film products may be rolled and stored for future use.

In yet another embodiment, the dried individual film products may be die cut, along with the substrate 20, to be packaged for distribution. Particularly in embodiments where the substrate 20 includes a pre-formed film thereon, cutting the dried individual film products may be useful, so as to form a cut multi-layered film product. Desirably, when the dried film products are to be cut from the substrate 20, the substrate 20 and any pre-formed film product thereon may not include any active component. As such, the leftover material from which the individual film products are cut may be discarded without wasting potentially expensive materials, including actives.

Figure 2:
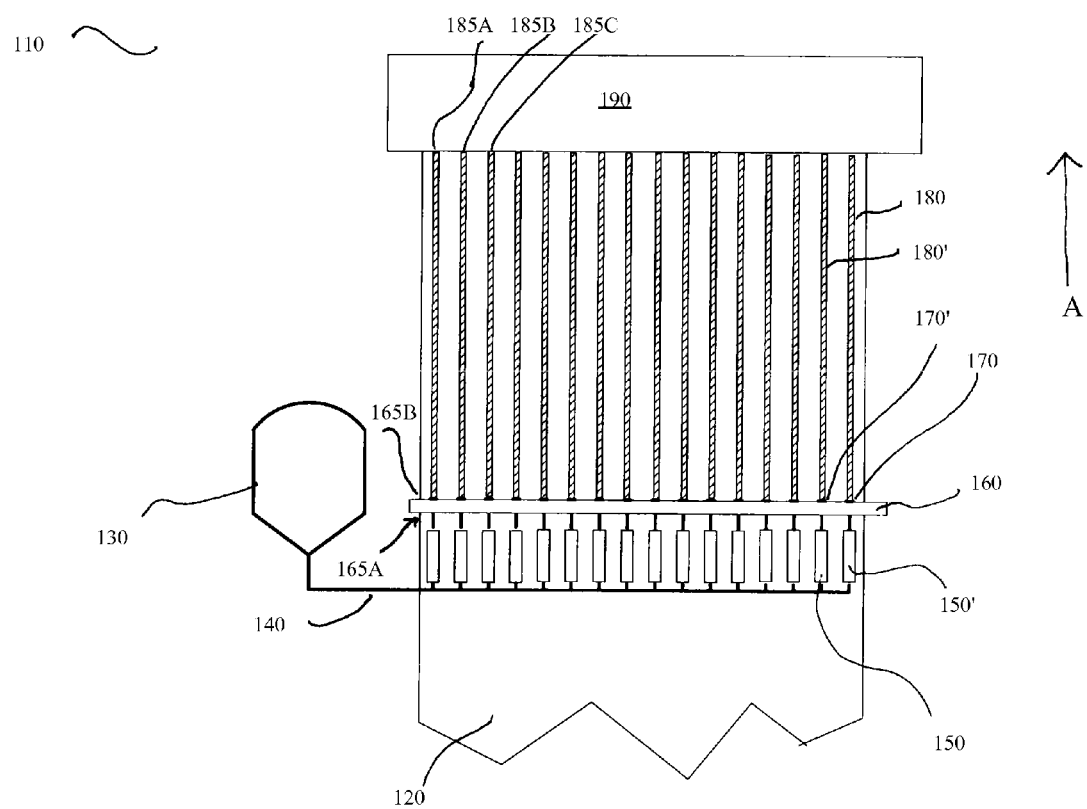
FIG. 2 is a depiction of a second embodiment of the present invention that is capable of forming individual film strips.

In an alternative embodiment, depicted in FIG. 2, the apparatus 110 may be used to form a continuous stripe or lane of film product 180. The formation of a continuous stripe of film product 180 may be useful, for example, in apparatuses that dispense a continuous roll of film, such as described above. Further, the formation of a continuous stripe of film product 180 may be beneficial for storage, packaging, and/or distribution purposes. As with above, the wet film strip products 180 are deposited onto a substrate 120, which may be a non-film substrate (i.e., mylar, paper, etc. as described above) or may include a pre-formed film thereon. The substrate 120 moves through the apparatus 110 as described above, in the direction marked by the arrow A.

The apparatus 110 includes a reservoir 130 as described above, which may be pressurized. The reservoir 130 is designed to house a film forming matrix. If desired, the reservoir 130 may include more than one compartment, thus being capable of housing various film forming components separately until just prior to formation of the film products, i.e., keeping solvents and polymers separately housed from active components.

A feed line 140 is in connection with the reservoir 130, and connects the reservoir 130 to a plurality of volumetric pumps 150, 150'. The volumetric pumps 150 may be any pumping mechanism desired, and preferably should be a pumping mechanism that allows for continuous and even dispensing of a wet film matrix therefrom. By dispensing an even and continuous amount of wet film matrix, uniform stripes of film product 180 may be formed on the surface of the substrate 120. It is particularly desired that each stripe of film product 180 include a substantially uniform amount of content per unit area, especially including a known amount of active per unit area. Each stripe 180 should have substantially the same thickness, width and viscosity, so as to provide a substantially uniform final film product. Thus, the volumetric pumps 150 should be capable of dispensing a substantially uniform and continuous amount of wet film product. In a desirable embodiment, volumetric film pumps 150 are gear pumps or metering pumps. Any known gear pumps and/or metering pumps in the art may be used.

There may be any number of volumetric pumps 150 in the apparatus 110, desirably arranged in a substantially side-by-side manner as shown in FIG. 2. Preferably, there is a space or gap between each volumetric pump 150, which aids in the processing and subsequent collection and packaging of the film products. The size of the gap between adjacent volumetric pumps 150 should be large enough to allow for ease of manufacture, but need not be so large that it reduces the number of pumps 150 available in the apparatus 110.

The number of volumetric pumps 150 dictates the number of stripes of film product 180 formed by the apparatus 110. For example, there may be between about 2 to about 30 volumetric pumps 150 in the apparatus, and more particularly between about 10 to about 20 volumetric pumps 150 in the apparatus. Each volumetric pump 150 is in fluid communication with the reservoir 130 via feed line 140, such that the film forming matrix is provided from the reservoir 130 to the pumps 150 on an even and continuous basis during operation. During operation, the amount of film forming matrix provided to the volumetric pump 150 located closest to the reservoir should be substantially equal to the amount of film forming matrix provided to the volumetric pump 150 located furthest from the reservoir. This ensures that the resulting stripes of film product 180 have substantially uniform content throughout the stripe 180.

Each volumetric pump 150 is associated with a first side 165A of a manifold 160, such that the film forming matrix may dispensed through the manifold 160. The manifold 160 includes a plurality of orifices 170 extending therethrough. The orifices 170 extend through the manifold 160 from the first side 165A to the second side 165B. In a preferred embodiment, each orifice 170 is in fluid communication with one volumetric pump 150, such that the film forming matrix may be dispensed from one volumetric pump 150 through one orifice 170. Thus, the number of orifices 170 should be equal to the number of volumetric pumps 150. In a desired embodiment, the orifices 170 are slot dies, but the orifices 170 may be any desired opening through which a wet film forming matrix may be fed. It is further desired that each orifice 170 be approximately the same size as each other, including approximately the same height, width, length and shape. In this fashion, the resulting stripe of film product 180 dispensed will each have a substantially uniform shape, size and content.

During use, the volumetric pumps 150 each dispense a wet film forming matrix through the manifold 160 via an orifice 170. The wet film forming matrix is deposited from the orifice 170 directly onto the surface of the substrate 120. During the processing, the substrate 120 is moved along the apparatus 110 in the direction A. It is particularly desirable to use volumetric pumps 150 that are capable of continuously dispensing the film forming matrix during the manufacturing process, so as to form a continuous stripe of film product 180.

The speed of movement of the substrate 120, in conjunction with the dispensing rate of the volumetric pumps 150, controls the amount of wet film forming matrix deposited onto the surface of the substrate 120. It may be desired that the substrate 120 move at a slow rate, for example, if the wet film forming matrix is highly viscous. Alternatively, it may be desired that the substrate 120 move at a faster rate, for example, if the wet film forming matrix is less viscous. The substrate 120 moves in the direction A from the manifold 160 to a drying apparatus 190, such as a drying oven or other means for drying the wet film matrix. The speed of the substrate 120 and the size of the drying apparatus 190 will dictate the length of time that the wet film product 180 is dried in the drying apparatus 190. For example, with a faster moving substrate 120 and/or a shorter drying apparatus 190, the wet film product 180 will be dried for a shorter length of time than it would with a slower moving substrate 120 and/or a longer drying apparatus 190.

The individual stripes of wet film products 180 are desirably arranged in columns (i.e., 185A, 185B, 185C) along the length of the surface of the substrate 120. It is particularly preferred that the stripes of wet film product 180 be arranged in a substantially side-by-side manner, with a sufficient space or gap between adjacent lane 185 to aid in the processing and subsequent collection/packaging of the film product. There may be as many columns 185 as is desired, with each column 185 being formed by an individual volumetric pump 150 and associated orifice 170. In addition, the space between each adjacent column 185 is approximately equal to the space between adjacent orifices 170 in the apparatus 110. Each column 185 of film material is desirably a continuously deposited lane of wet film matrix, such that, after drying is complete, the individual column 185 of dried film product may be collected and packaged. For example, it may be desired that the individual column 185 be removed from the substrate 120 and rolled, where it may be housed in a dispensing apparatus for use by an end user. Alternatively, the column 185 may be cut along with the substrate 120 to provide a continuous stripe 185 of film with a substrate backing. Further, the stripe 180 of dried film may be cut into individual film products of approximately equal size and shape, each individual film product being one dosage unit.

Figure 3A:
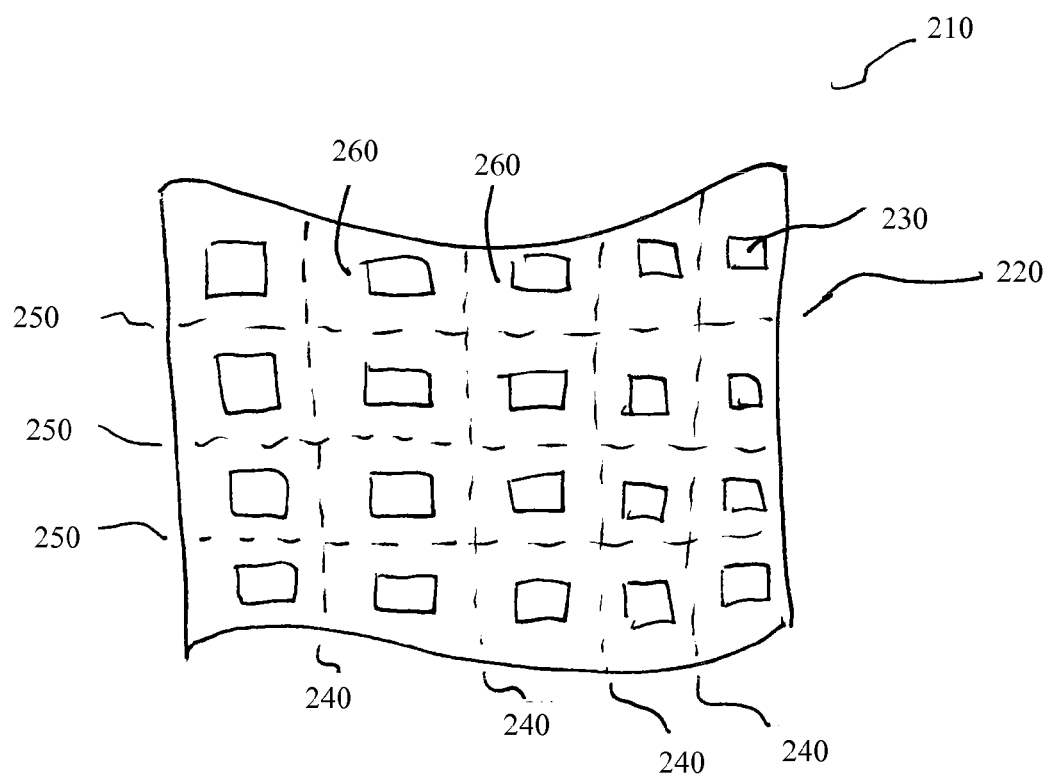
FIGS. 3A and 3B are depictions of film patches formed by an alternate embodiment of the present invention.
Figure 3B:
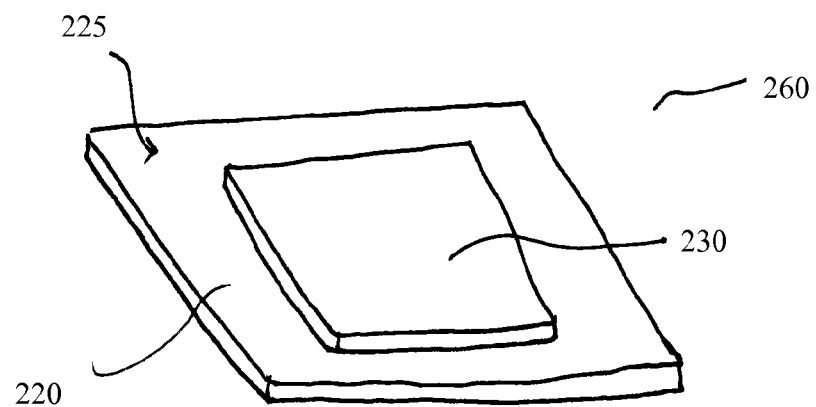

In one particular embodiment as depicted in FIGS. 3A and 3B, the apparatus may be useful in forming a series of individual, multi-layered products. For example, the individual multi layered products may include active-containing patches. The apparatus represented by FIG. 1 and described above is particularly useful in forming individual, multi-layered products, such as patches. In this embodiment, the substrate 210 may include a sheet of ingestible and/or dissolvable film 220 (also referred to herein as a "first layer"), which forms a backing layer for an active-containing layer. In some embodiments, the sheet of ingestible film 220 may be the substrate 210, such as if the sheet of ingestible film 220 is self-supporting and capable of being fed through the apparatus itself. It is preferable that the first layer 220 be made of a mucoadhesive, biocompatible, dissolvable material. It may be desired that the first layer 220 is a slow-dissolving film sheet. By "slow-dissolving", it is intended that the sheet 220 has a longer dissolution rate than the rate of the active-containing layer (described below) adhered thereto. The first layer 220 may be formed on a separate substrate, such as mylar, paper, or other non-ingestible backing layer described above. The first layer 220 may be pre-formed and dried, it may be undried, or it may be partially dried. For example, the first layer 220 may be a visco-elastic mass of film-forming material.

The first layer 220 has a first surface 225. During processing, as described above, a plurality of individual active-containing wet film layers 230 (also referred to herein as a "second layer") are deposited onto the first surface 225 of the first layer 220. Desirably, the active-containing wet film layers 230 are made of a biocompatible polymeric material, which dissolves at a faster rate than the first layer 220. As explained above, the active-containing wet film layers 230 are desirably deposited through a plurality of volumetric pumps in a substantially side-by-side manner, with a desired gap between adjacent active-containing wet film layers 230.

After the individual active-containing film layers 230 have been deposited onto the first layer 220 and dried, the two layers (220, 230) should be sufficiently adhered to each other such that they do not become separated. The drying process alone may sufficiently adhere the two layers 220, 230 to each other, or there may be an adhesive composition applied between the first layer 220 and the active-containing film layer 230.

Once the active-containing film layer 230 (and the first layer 220, if necessary) has been sufficiently dried, the first layer 220 may be sized and cut. In one embodiment, the sheet of dissolvable film 220 is cut in a first direction 240 (between adjacent active containing film layers 230) and in a second direction 250 (between adjacent active containing film layers 230) that is substantially perpendicular to the first direction 240, so as to form a series of individual multi-layered products 260. As can be seen in FIG. 3B, the multi-layered product 260 includes a first layer 220 and second layer 230 adhered thereto. The first layer 220 is desirably slower-dissolving than the second layer 230. The second layer 230 desirably includes at least one active component. If desired, the first layer 220 may include at least one active component, which may be the same or different than the active component in the second layer 230.

In one embodiment, it is preferred that the second layer 230 be sized smaller than the first layer 220, i.e., that the length and/or width of the second layer 230 be smaller than the length and/or width of the first layer 220 with which it is associated. In this fashion, at least a portion of the first side 225 of the first layer 220 is exposed beyond the sides of the second layer 230. It is especially preferred that a portion of the first side 225 of the first layer 220 is exposed around the entire periphery of the second layer 230. For example, as depicted in FIG. 3B, the second layer 230 may have a smaller length and width than the first layer 220, and the second layer may be deposited generally in the center of the first layer 220. Thus, the first side 225 of the first layer 220 is exposed around the entire periphery of the second layer 230. Alternatively, the width and/or length of the first layer 220 and second layer 230 may be approximately equal. In another embodiment, one or more sides of the first layer 220 and second layer 230 may be flush with each other.

It is preferable that at least the first side 225 of the first layer 220 be made of a mucoadhesive material, such that it may be sufficiently applied to a mucosal surface of the body of the user and adhere thereto. For example, the resulting multi-layer product 260 may be applied to any skin surface of a user, such as, for example, a mucosal surface, including oral, nasal, optical, vaginal, or anal surfaces of the user, or may be applied to an internal body organ such as during surgery. In this embodiment, the individual multi-layered product 260 may be applied by a user to a skin surface, such that the first side 225 of the first layer 220 is in contact with the skin surface and substantially adhered thereto. In this embodiment, the active-containing layer 230 is directed towards the skin surface of the user. If the second layer 230 dissolves at a faster rate than the first layer 220, the second layer 230 may be allowed to fully dissolve in the direction of the skin surface of the user, allowing full absorption of any active(s) contained in the second layer 230 into the user's body.

It will be understood, of course, that the multi-layered film product embodiment described above may be formed with a continuous stripe of active-containing film product (as depicted in FIG. 2 and described above), as opposed to individual active-containing film layers 230. In such an embodiment, the product may be cut in such a fashion such that two opposing sides of the first surface 225 of the first layer 220 are exposed beyond the stripe of second layer.

Figure 4:
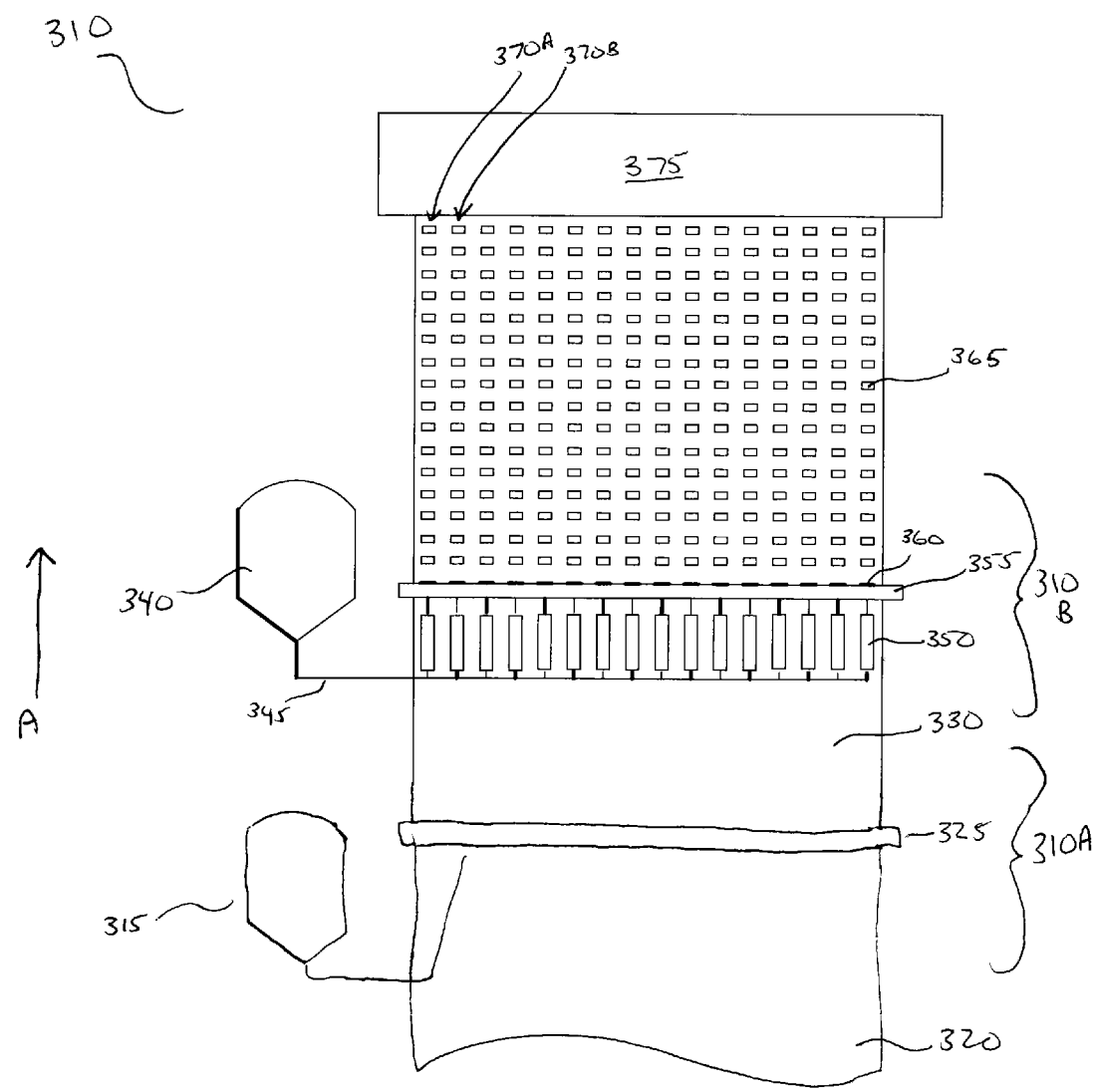
FIG. 4 is a depiction of a further embodiment of the present invention that is capable of forming a substrate and a plurality of individual film products on the surface of the substrate.

In another embodiment depicted in FIG. 4, the apparatus 310 may include a first film-forming region 310A and a second film-forming region 310B. In such embodiments, the first film forming region 310A may include a first reservoir 315, which houses a first film forming matrix. The first film forming matrix generally includes film-forming components as described above, and may include an active or it may be active-free. The apparatus 310 includes a substrate 320, which is made from a non-ingestible material, such as mylar, paper, and other materials described above. The substrate 320, as with other embodiments described above, moves through the apparatus 310 in the direction represented by the arrow A, i.e., from the first film forming region 310A to the second film forming region 310B. The first film forming region 310A includes a first manifold 325, which is in fluid connection with the first reservoir 315, and is intended to deposit a continuous sheet 330 of first film forming material onto the substrate 320 during use. Optionally, there may be a first drying apparatus (not shown) disposed at a location after the first manifold 325 but before the second film-forming region 310B.

During use, the apparatus 310 deposits the sheet 330 of first film forming material onto the substrate 320, forming a first layer of film forming material. It may be desired that the sheet 330 of first film forming material be immediately dried before entering the second film forming region 310B. Alternatively, the sheet 330 of first film forming material may be partially dried before entering the second film forming region 310B, for example, to form a visco-elastic mass of film material.

The first layer of film forming material 330 (whether dried, undried, or partially dried) travels through the apparatus 310 into the second film forming region 310B. The second film forming region 310B may include the components and methods described above with respect to the embodiments depicted in FIG. 1 or 2. For example, the second film forming region 310B includes a second reservoir 340, which is in fluid communication with a second feed line 345. The second feed line 345 is in communication with a plurality of volumetric pumps 350. The plurality of volumetric pumps 350 is in communication with a second manifold 355, which includes a plurality of orifices 360. As explained above, desirably, each orifice 360 is associated with one volumetric pump 350. The second film forming region 310 deposits a plurality of wet film products 365 onto the first layer of film forming material 330 in a substantially side-by-side manner in a series of columns (i.e., 370A, 370B).

The first layer of film material 330 and the plurality of wet film products 365 travel through the apparatus 310 into a drying apparatus 375, which may be a drying oven. The wet film products 365 (and the first layer of film, if necessary) are dried, such as by the drying methods described above.

Once sufficiently dried, the resulting multi-layered film products (including the first layer 330 and the plurality of now-dried film products 365) may be sized and cut as desired, or alternatively may be stored for future use. The first layer 330 and film products 365 are desirably adhered to each other, which may be achieved simply through the drying process or there may be an adhesive composition applied between the first layer 330 and the film products 365 prior to deposition thereof.

The present invention takes into account, and is premised on the understanding of, a number of issues that may adversely impact the flow of material through a slot die, which may result in changes in flow of the material. Slight changes in certain parameters may undesirably alter the content uniformity of the resulting film, in particular the uniformity of active, which is produced across a plurality of slot dies fed from a single pump. Uniformity of content among individual films or dosages, particularly uniformity of active, is especially important in film manufacturing. The present invention minimizes or all together eliminates the potential problems associated with use of a single pump, as will be explained below.

In typical systems and in the present invention, a preferred slot die is a rectangular orifice having three dimensions: height (B), width (W) and length (L). The length (L) is understood to be the length of the orifice from the front of the die to the back, depicted in FIG. 1 as the length from the first side 65A and a second side 65B. The flow through a rectangular die, such as the slot die of the present invention, may be defined by the Hagen-Poiseuille equation:

$$Q = \frac{2}{3} \frac{(P_0 - P_L)B^3 W}{\mu L}$$

In the above equation, Q is the volumetric flow rate, P is the pressure, and $\mu$, is the viscosity of the fluid being flowed through the die. When multiple orifices are being flowed through in typical apparatuses, such as a slot die coater with a single pump feeding a manifold with multiple slot dies, the flow rate may be adversely impacted by many factors. Even slight variations in these factors may have a significant impact in the flow rate, and thus the content of films formed by the apparatus. The potential adverse impact of such a system is reduced or eliminated through the present invention.

For example, pressure changes may impact the flow rate, since flow is proportional to the pressure at the entrance to the slot in the slot die. If a substantially uniform flow across multiple slot dies is desired, it is important to have a substantially equal pressure level at the entrance to each slot die. To achieve this equal pressure level across all dies, a manifold design with one single pump feeding to it must prevent the flow inside the manifold from being disturbed by external forces. That is, the flow within such a manifold must not be disturbed by changes in temperature, viscosity, or non-uniform dispersions or clumping of components in the fluid being flowed.

In addition, the height of the slot die may have an affect on the flow rate of the fluid being flowed through. Flow is proportional to the height of the slot, which is typically the narrowest dimension of the slot die, to the third power. Since this is typically the smallest dimension, any variability in this dimension from slot to slot will have a potentially high impact on the percentage of variability in the flow rate of the matrix as it is fed to each of the slot dies. To counter this problem, it would be critical that each of the slot dies in the apparatus have the same height dimension as each other. Even a 3% difference in height between adjacent slot dies in the apparatus would result in a nearly 10% variation in flow rate.

Another factor that may affect the flow rate is the viscosity of the fluid being flowed through the dies. Flow rate is inversely proportional to the viscosity, such that changes in the localized viscosity due to forces such as temperature or non-homogeneity (clumping of particles in the matrix) will impact the flow rate through that slot, and subsequently the flow rate through to the remaining slot dies. Even a slight change in the flow rate may adversely affect the uniformity of content, including active content, of the films formed by subsequent slot dies.

In the present invention, the flow rate through each individual slot die is determined and controlled by the flow exiting the individual volumetric pump attached to an individual slot die. The present invention overcomes the above problems by using a plurality of individual pumps associated with individual slot dies. The pressure may be kept at a substantially constant level among each individual pump. In addition, since each slot die is associated with an individual pump, variations in the height between adjacent slot dies will have no affect on each other. Finally, use of individual pumps may easily take into account viscosity changes and minimize any potential affect based on variations therein.

While the above problems may potentially be solved through the use of a single pump-fed manifold directed to a plurality of individual slot dies, such an apparatus would need to include: a manifold that is not affected by any external forces; identical slot dies; and a viscosity of the flowed matrix that is completely uniform with no drop in viscosity from the first slot die to the last slot die. Such an apparatus would be cumbersome and difficult to achieve.

As can be appreciated by those of skill in the art, the present invention substantially solves the problems associated with such single-pump apparatuses by providing a system and method that provides each slot die with its own individual pump. The present system allows for greater control and stability between and among the slot dies in the system. The potential issues set forth in the Hagen-Poiseuille equation above are rectified with the present invention in an efficient and controlled manner. The result is a more predictable and uniform product among each slot die in the system.

A number of embodiments of the invention have been described. Nevertheless, it will be understood that various modifications may be made without departing from the spirit and scope of the invention. Further, the steps described above may be modified in various ways or performed in a different order than described above, where appropriate. Accordingly, alternative embodiments are within the scope of the disclosure.

What is claimed is:

1. A method of forming a plurality of individual film products, comprising the steps of:
   (a) providing a reservoir housing a film forming matrix;
   (b) providing a plurality of individual volumetric pumps connected to said reservoir;
   (c) providing a manifold comprising a plurality of orifices, wherein said manifold comprises a first side and a second side, wherein each orifice extends from said first side of said manifold to said second side of said manifold, wherein each orifice is in fluid communication on said first side of said manifold with one of said individual volumetric pumps which is its own individual volumetric pump;
   (d) feeding said film forming matrix from said reservoir to said individual volumetric pumps; and thereafter
   (e) dispensing a predetermined amount of said film forming matrix from each of said individual volumetric pumps through said orifice in fluid communication therewith from said first side of said manifold to said second side of said manifold; and thereafter
   (f) depositing a plurality of individual wet film products directly onto a substrate from each of said orifices.

2. The method of claim 1, wherein said substrate is a backing film.

3. The method of claim 1, wherein said substrate moves in a first direction from said plurality of orifices to a drying apparatus.

4. The method of claim 3, wherein the drying apparatus is a drying oven.

5. The method of claim 1, wherein said substrate is continuously moved in a first direction from said plurality of orifices to a drying apparatus.

6. The method of claim 5, wherein the drying apparatus is a drying oven.

7. The method of claim 1, wherein steps (d)-(f) are repeated.

8. The method of claim 7, wherein an individual wet film product is extruded onto a region of said substrate onto which no individual wet film product has already been extruded.

9. The method of claim 1, wherein each of said individual volumetric pumps dispenses about 4 microliters to about 250 microliters per stroke.

10. The method of claim 1, wherein said film forming matrix is at least 25% solids.

11. The method of claim 1, further comprising the step:
(g) drying said plurality of individual wet film products to form a plurality of dried individual film products.

12. The method of claim 11, wherein said plurality of dried individual film products are die cut.

13. The method of claim 11, wherein each of the dried individual film products is about 1000 mg or less.

14. The method of claim 1, wherein said individual volumetric pumps are piston pumps.

15. The method of claim 1, wherein said individual volumetric pumps are variable speed piston pumps.

16. The method of claim 1, wherein said individual volumetric pumps are variable stroke piston pumps.

17. The method of claim 1, wherein said individual volumetric pumps are dual piston pumps.

18. The method of claim 1, wherein each of said orifices is a slot die.

19. The method of claim 1, wherein said individual film products are for the delivery of a desired amount of an active, and wherein each individual wet film product comprises an active in an amount which varies by no more than about 10% from said desired amount of said active.

20. The method of claim 1, wherein the film forming matrix is extruded through said orifice in step (e).

21. The method of claim 1, wherein each of the individual wet film products is about 2000 mg or less.

22. The method of claim 1, wherein the substrate is for packaging the individual film products.

23. The method of claim 1, wherein the reservoir is pressurized.

24. The method of claim 1, wherein the individual volumetric pumps are connected to the reservoir by a feed line.

25. A method of forming a plurality of individual film strips, comprising the steps of:
(a) providing a reservoir housing a film forming matrix;
(b) providing a plurality of individual metering pumps connected to said reservoir;
(c) providing a manifold comprising a plurality of orifices, wherein said manifold comprises a first side and a second side, wherein each orifice extends from said first side of the manifold to said second side of said manifold, wherein each orifice is in fluid communication on said first side of said manifold with one of said individual metering pumps which is its own individual metering pump;
(d) feeding said film forming matrix from said reservoir to said plurality of individual metering pumps; and thereafter
(e) dispensing a predetermined amount of said film forming matrix from each of said individual metering pumps through said orifice in fluid communication therewith; and thereafter
(f) depositing a plurality of individual wet film strips directly onto a substrate from each of said orifices.

26. The method of claim 25, wherein said substrate is a backing film.

27. The method of claim 25, wherein said substrate is continuously moved in a first direction from said plurality of orifices to a drying apparatus.

28. The method of claim 27, wherein the drying apparatus is a drying oven.

29. The method of claim 25, wherein an individual wet film strip is extruded onto a region of said substrate onto which no wet film strip has been extruded.

30. The method of claim 25, wherein said film forming matrix is at least 25% solids.

31. The method of claim 25, further comprising the step:
(g) drying said individual wet film strips to form a plurality of dried individual film strips.

32. The method of claim 31, wherein at least one dried individual film strip is rolled and stored for future use.

33. The method of claim 31, wherein at least one dried individual film strip may be cut into individual film products.

34. The method of claim 31, wherein each of the dried individual film strips is about 1000 mg or less.

35. The method of claim 25, wherein each of said orifices is a slot die.

36. The method of claim 25, wherein each of said individual wet film strips is extruded into a narrow stripe on said substrate.

37. The method of claim 25, wherein said individual wet film strips are for the delivery of a desired amount of an active, and wherein each individual wet film strip comprises an active in an amount which varies by no more than about 10% from said desired amount of said active.

38. The method of claim 25, wherein the film forming matrix is extruded through said orifice in step (e).

39. The method of claim 25, wherein each of the individual wet film strips is about 2000 mg or less.

40. The method of claim 25, wherein the substrate is for packaging the individual film strips.

41. The method of claim 25, wherein the reservoir is pressurized.

42. The method of claim 25, wherein the individual metering pumps are connected to the reservoir by a feed line.

43. An apparatus for forming a plurality of individual film products, comprising:
(a) a reservoir for housing a film forming matrix;
(b) a plurality of individual volumetric pumps connected to said reservoir;
(c) a manifold comprising a plurality of orifices, wherein said manifold comprises a first side and a second side, wherein each orifice extends from the first side of the manifold to the second side of the manifold, wherein each orifice is in fluid communication on said first side of said manifold with one of said individual volumetric pumps which is its own individual volumetric pump;
(d) a substrate; and
(e) a means for moving said substrate through said apparatus.

44. The apparatus of claim 43, wherein said reservoir is pressurized.

45. The apparatus of claim 43, wherein said individual volumetric pumps are rotating piston pumps.

46. The apparatus of claim 43, wherein each individual volumetric pump discharges about 4 microliters to about 250 microliters per stroke.

47. The apparatus of claim 43, wherein each individual volumetric pump has a varying stroke capacity.

48. The apparatus of claim 43, wherein each individual volumetric pump has a varying speed capacity.

49. The apparatus of claim 43, wherein the individual film products are small film products.

50. The apparatus of claim 43, further comprising a drying apparatus.

51. The apparatus of claim 50, wherein the drying apparatus is a drying oven.

52. The apparatus of claim 43, wherein each of said orifices is a slot die.

53. The apparatus of claim 43, wherein the individual film products are wet individual film products which are each about 2000 mg or less.

54. The apparatus of claim 43, wherein the individual film products are dried individual film products which are each about 1000 mg or less.

55. The apparatus of claim 43, wherein the substrate is for packaging the individual film products.

56. The apparatus of claim 43, wherein the individual volumetric pumps are connected to the reservoir by a feed line.

57. A method of forming a plurality of individual film patches, comprising the steps of:
(a) providing a substrate comprising a sheet comprising a dissolvable polymeric material, said sheet having a top surface, wherein said substrate continuously moves in a first direction;
(b) providing a reservoir housing a wet film forming matrix, said wet film forming matrix comprising a second polymeric material and an active;
(c) providing a plurality of individual volumetric pumps connected to said reservoir;
(d) providing a manifold comprising a plurality of orifices, wherein said manifold comprises a first side and a second side, wherein each orifice extends from the first side of the manifold to the second side of the manifold, wherein each orifice is in fluid communication on said first side of said manifold with one of said individual volumetric pumps which is its own individual volumetric pump, wherein each orifice is separated from each other by a gap;
(e) feeding said wet film forming matrix from said reservoir to said individual volumetric pumps; and thereafter
(f) dispensing a predetermined amount of said film forming matrix from each of said volumetric pumps through said orifice in fluid communication therewith from said first side of said manifold to said second side of said manifold; and thereafter
(g) depositing said predetermined amount of said wet film forming matrix directly onto said top surface of said sheet from each of said orifices to form a plurality of wet film products; and
(h) drying said wet film products to form a plurality of multi-layer film patches comprising a first layer comprising said sheet and a second layer comprising a dried film product.

58. The method of claim 57, wherein steps (e)-(g) are repeated.

59. The method of claim 57, wherein said first layer has a slower rate of dissolution than said second layer.

60. The method of claim 57, further comprising the step:
(i) cutting said first layer to provide an individual film patch, wherein said individual film patch comprises one dried film product.

61. The method of claim 60, wherein a top surface of said first layer of said individual film patch has either a larger width or a larger length than said second layer, and wherein at least a portion of said top surface of said first layer is not in contact with said second layer.

62. The method of claim 61, further comprising the step:
(j) placing said individual film patch onto the skin of a user, wherein said second layer is in contact with the user's skin and wherein at least a portion of said top surface of said first layer is in contact with the user's skin.

63. The method of claim 61, further comprising the step:
(j) placing said individual film patch onto the mucosal tissue of a user, wherein said second layer is in contact with the user's skin and wherein at least a portion of said top surface of said first layer is in contact with the user's skin.

64. The method of claim 57, wherein the film forming matrix is extruded through said orifice in step (f).

65. The method of claim 57, wherein each of the wet film products is about 2000 mg or less.

66. The method of claim 57, wherein the dried film product is about 1000 mg or less.

67. The method of claim 57, wherein the sheet comprising a dissolvable polymeric material is present on a packaging substrate.

68. The method of claim 57, wherein the sheet comprising a dissolvable polymeric material further comprises an active.

69. The method of claim 57, wherein the reservoir is pressurized.

70. The method of claim 57, wherein the individual volumetric pumps are connected to the reservoir by a feed line.

71. A method of forming a plurality of individual film products, comprising the steps of:
(a) providing a reservoir housing a film forming matrix comprising at least one polymer, at least one solvent, and a desired amount of at least one active;
(b) providing a plurality of individual volumetric pumps connected to said reservoir;
(c) providing a manifold comprising a first side, a second side, and a plurality of orifices, wherein each orifice extends from the first side of the manifold to the second side of the manifold and wherein each orifice is in fluid communication with one of said individual volumetric pumps on said first side of said manifold;
(d) feeding said film forming matrix from said reservoir to said individual volumetric pumps; and thereafter
(e) dispensing a predetermined amount of said film forming matrix from each of said volumetric pumps through said orifice in fluid communication therewith from said first side of said manifold to said second side of said manifold; and thereafter
(f) depositing a plurality of individual wet film products directly onto a substrate from each of said orifices; wherein the amount of active in each of the individual wet film products varies by no more than about 10% from said desired amount of said active.

72. The method of claim 71, further comprising the step:
(g) drying said plurality of individual wet film products to form a plurality of dried individual film products.

73. The method of claim 72, wherein each of the dried individual film products is about 1000 mg or less.

74. The method of claim 71, wherein each of the individual wet film products is about 2000 mg or less.

75. The method of claim 71, wherein the substrate is for packaging the individual film products.

76. The method of claim 71, wherein the reservoir is pressurized.

77. The method of claim 71, wherein the individual volumetric pumps are connected to the reservoir by a feed line.

* * * * *